US011116892B2

(12) United States Patent
Brady et al.

(10) Patent No.: US 11,116,892 B2
(45) Date of Patent: Sep. 14, 2021

(54) MEDIUM INJECTION DIVERSION AND MEASUREMENT

(71) Applicant: Osprey Medical, Inc., Minnetonka, MN (US)

(72) Inventors: Dale Brady, New Brighton, MN (US); Rodney L. Houfburg, Prior Lake, MN (US); William Burmaster, Plymouth, MN (US)

(73) Assignee: Osprey Medical, Inc., Minnetonka, MN (US)

( * ) Notice: Subject to any disclaimer, the term of this patent is extended or adjusted under 35 U.S.C. 154(b) by 0 days.

(21) Appl. No.: 16/024,768

(22) Filed: Jun. 30, 2018

(65) Prior Publication Data

US 2018/0318495 A1 Nov. 8, 2018

Related U.S. Application Data

(63) Continuation-in-part of application No. 15/089,061, filed on Apr. 1, 2016, which is a continuation-in-part
(Continued)

(51) Int. Cl.
*A61M 5/00* (2006.01)
*A61M 5/168* (2006.01)
(Continued)

(52) U.S. Cl.
CPC .......... *A61M 5/007* (2013.01); *A61M 5/1408* (2013.01); *A61M 5/16813* (2013.01);
(Continued)

(58) Field of Classification Search
CPC ........ A61M 5/484; A61M 5/488; A61M 5/48; A61M 5/14; A61M 5/16809;
(Continued)

(56) References Cited

U.S. PATENT DOCUMENTS 3,469,578 A 9/1969 Bierman
3,543,759 A 12/1970 McWhorter
(Continued)

FOREIGN PATENT DOCUMENTS

DE 19643813 4/1998
EP 523343 1/1993
(Continued)

OTHER PUBLICATIONS

US 7,559,463 B2, 07/2009, Hickle (withdrawn)
(Continued)

*Primary Examiner* — Nilay J Shah

(57) ABSTRACT

A system for measurement automation of a fluid injected into a patient includes a reservoir, a fluid injection apparatus, and a measurement automation apparatus. The fluid injection apparatus includes a delivery conduit, an injector for injecting the fluid into the patient, a diverter assembly disposed between the delivery conduit and the injector, and a connector between the diverter assembly and delivery conduit. The diverter assembly is configured to divert at least a portion of the fluid away from an injection fluid path between the injector and the delivery conduit to the reservoir. The measurement automation apparatus includes an injector sensor module, a reservoir sensor module, a processor configured to receive the data from the sensor modules, and a display.

20 Claims, 20 Drawing Sheets

Related U.S. Application Data of application No. 14/851,958, filed on Sep. 11, 2015, now Pat. No. 10,022,497, said application No. 15/089,061 is a continuation-in-part of application No. 14/222,331, filed on Mar. 21, 2014, now Pat. No. 9,999,718, which is a continuation-in-part of application No. 13/975,052, filed on Aug. 23, 2013, now Pat. No. 10,413,677, said application No. 14/851,958 is a continuation-in-part of application No. 13/839,771, filed on Mar. 15, 2013, now Pat. No. 9,320,846, said application No. 13/975,052 is a continuation-in-part of application No. 13/839,771, filed on Mar. 15, 2013, now Pat. No. 9,320,846.

(60) Provisional application No. 62/527,919, filed on Jun. 30, 2017, provisional application No. 62/141,723, filed on Apr. 1, 2015, provisional application No. 62/082,260, filed on Nov. 20, 2014, provisional application No. 62/048,974, filed on Sep. 11, 2014, provisional application No. 61/697,137, filed on Sep. 5, 2012, provisional application No. 61/694,137, filed on Aug. 28, 2012.

(51) Int. Cl.
*A61M 5/14* (2006.01)
*A61M 5/172* (2006.01)
*A61M 5/315* (2006.01)
*A61M 5/145* (2006.01)

(52) U.S. Cl.
CPC ........ *A61M 5/16886* (2013.01); *A61M 5/172* (2013.01); *A61M 5/31568* (2013.01); *A61M 5/31573* (2013.01); *A61M 5/1452* (2013.01); *A61M 5/1684* (2013.01); *A61M 2205/3306* (2013.01); *A61M 2205/3317* (2013.01); *A61M 2205/3379* (2013.01); *A61M 2205/3389* (2013.01); *A61M 2205/50* (2013.01); *A61M 2205/502* (2013.01)

(58) Field of Classification Search
CPC .............. A61M 5/31568; A61M 5/204; A61M 5/1684; A61M 5/482; A61M 5/1413; A61M 5/16804; A61M 5/16881; A61M 3/005; A61M 5/16827; A61M 5/2066; A61M 2005/3114; A61M 2205/3306
See application file for complete search history.

(56) References Cited

U.S. PATENT DOCUMENTS

| | | |
|---|---|---|
| 3,556,122 A | 1/1971 | Laerdal |
| 3,572,375 A | 3/1971 | Rosenberg |
| 3,626,978 A | 12/1971 | Hoekstra |
| 3,633,613 A | 1/1972 | Julow |
| 3,661,174 A | 5/1972 | Cripe |
| 3,695,575 A | 10/1972 | Hauser |
| 3,818,929 A | 6/1974 | Braukmann |
| 3,905,382 A | 9/1975 | Waterston |
| 3,941,149 A | 3/1976 | Mittleman |
| 3,958,573 A | 5/1976 | Wiley |
| 3,985,141 A | 10/1976 | Stanley et al. |
| 4,000,741 A | 1/1977 | Binard et al. |
| 4,006,736 A | 2/1977 | Kranys et al. |
| 4,030,497 A | 6/1977 | Binard et al. |
| 4,044,793 A | 8/1977 | Krueger et al. |
| 4,074,714 A | 2/1978 | Binard et al. |
| 4,077,405 A | 3/1978 | Haerten et al. |
| 4,084,606 A | 4/1978 | Mittleman |
| 4,136,708 A | 1/1979 | Cosentino et al. |
| 4,142,525 A | 3/1979 | Binard et al. |
| 4,147,170 A | 4/1979 | Taylor |
| 4,240,430 A | 12/1980 | Binard et al. |
| 4,289,006 A | 9/1981 | Hallengren |
| 4,318,400 A | 3/1982 | Peery et al. |
| 4,329,985 A | 5/1982 | Bonchek |
| 4,381,006 A | 4/1983 | Genese |
| 4,392,847 A | 7/1983 | Whitney et al. |
| 4,403,988 A | 9/1983 | Binard et al. |
| 4,457,751 A | 7/1984 | Rodler |
| 4,481,008 A | 11/1984 | Kurtz |
| 4,501,291 A | 2/1985 | Siegrist |
| 4,502,502 A | 3/1985 | Krug |
| 4,550,747 A | 11/1985 | Woodworth et al. |
| 4,602,700 A | 7/1986 | Szabo |
| 4,655,746 A | 4/1987 | Daniels et al. |
| 4,671,786 A | 6/1987 | Krug |
| 4,744,786 A | 5/1988 | Hooven |
| 4,755,172 A | 7/1988 | Baldwin |
| 4,758,223 A | 7/1988 | Rydell |
| 4,795,431 A | 1/1989 | Walling |
| 4,813,937 A | 3/1989 | Vaillancourt |
| 4,838,857 A | 6/1989 | Strowe et al. |
| 4,845,493 A | 7/1989 | Howard |
| 4,867,743 A | 9/1989 | Vaillancourt |
| 4,997,420 A | 3/1991 | LeFevre |
| 5,059,174 A | 10/1991 | Vaillancourt |
| 5,094,148 A | 3/1992 | Haber et al. |
| 5,139,484 A | 8/1992 | Hazon et al. |
| 5,167,631 A | 12/1992 | Thompson et al. |
| 5,273,187 A | 11/1993 | Suzuki |
| 5,376,785 A | 12/1994 | Chin et al. |
| 5,460,609 A | 10/1995 | O'Donnell |
| 5,534,691 A | 7/1996 | Holdaway et al. |
| 5,556,386 A | 9/1996 | Todd |
| 5,573,515 A | 11/1996 | Wilson et al. |
| 5,575,767 A | 11/1996 | Stevens |
| 5,662,612 A | 9/1997 | Niehoff |
| 5,681,285 A | 10/1997 | Ford |
| 5,685,851 A | 11/1997 | Murphy et al. |
| 5,707,356 A | 1/1998 | Paul |
| 5,752,940 A | 5/1998 | Grimard |
| 5,785,681 A | 7/1998 | Indravudh |
| 5,792,117 A | 8/1998 | Brown |
| 5,799,700 A | 9/1998 | Teh et al. |
| 5,800,397 A | 9/1998 | Wilson et al. |
| 5,806,519 A | 9/1998 | Evans, III et al. |
| 5,807,321 A * | 9/1998 | Stoker ............... A61M 5/16809 604/251 |
| 5,827,941 A | 10/1998 | Good et al. |
| 5,840,026 A | 11/1998 | Uber, III et al. |
| 5,840,071 A | 11/1998 | Kriesel et al. |
| 5,882,338 A | 3/1999 | Gray |
| 5,882,343 A | 3/1999 | Wilson et al. |
| 5,885,216 A | 3/1999 | Evans, III et al. |
| 5,916,165 A | 6/1999 | Duchon et al. |
| 5,954,700 A | 9/1999 | Kovelman |
| 6,019,747 A | 2/2000 | McPhee |
| 6,086,559 A | 7/2000 | Enk |
| 6,113,578 A | 9/2000 | Brown |
| 6,159,180 A | 12/2000 | Kriesel et al. |
| 6,270,481 B1 * | 8/2001 | Mason ................ A61M 5/1424 604/181 |
| 6,317,623 B1 | 11/2001 | Griffiths et al. |
| 6,397,098 B1 | 5/2002 | Uber, III et al. |
| 6,409,699 B1 | 6/2002 | Ash |
| 6,442,418 B1 | 8/2002 | Evans, III et al. |
| 6,558,125 B1 | 5/2003 | Futterknecht |
| 6,645,177 B1 * | 11/2003 | Shearn ................ A61M 5/1456 604/155 |
| 6,850,792 B2 | 2/2005 | Ohishi |
| 6,858,020 B2 | 2/2005 | Rusnak |
| 6,866,654 B2 | 3/2005 | Callan et al. |
| 6,889,074 B2 | 5/2005 | Uber, III et al. |
| 6,901,283 B2 | 5/2005 | Evans, III et al. |
| 6,966,893 B2 | 11/2005 | Holtby et al. |
| 6,969,353 B2 | 11/2005 | Brock-Fisher et al. |
| 6,970,735 B2 | 11/2005 | Uber, III et al. |
| 7,022,107 B1 | 4/2006 | Christensen et al. |
| 7,065,395 B2 | 6/2006 | Lienard et al. |

(56) References Cited

U.S. PATENT DOCUMENTS

| | | | |
|---|---|---|---|
| 7,094,216 | B2 | 8/2006 | Trombley, III et al. |
| 7,255,684 | B2 | 8/2007 | Zubry |
| 7,270,648 | B2 | 9/2007 | Kazemzadeh |
| 7,326,186 | B2 | 2/2008 | Trombley, III et al. |
| 7,470,253 | B2 | 12/2008 | Kriesel et al. |
| 7,516,760 | B2 | 4/2009 | Weber |
| 7,611,503 | B2 | 11/2009 | Spohn et al. |
| 7,618,412 | B2 | 11/2009 | Chernack |
| 7,678,070 | B2 | 3/2010 | Kumar et al. |
| 7,766,885 | B2 | 8/2010 | Olsen |
| 7,815,604 | B2 | 10/2010 | Massengale et al. |
| 7,854,726 | B2 | 12/2010 | Fago et al. |
| 7,925,330 | B2 | 4/2011 | Kalafut et al. |
| 7,927,305 | B2 | 4/2011 | Yribarren et al. |
| 7,951,129 | B2 | 5/2011 | Chinchoy |
| 7,955,301 | B1 | 6/2011 | McKay |
| 8,075,490 | B2 | 12/2011 | Lofgren et al. |
| 8,147,448 | B2 | 4/2012 | Sundar et al. |
| 8,172,790 | B2 | 5/2012 | Hunter et al. |
| 8,197,443 | B2 | 6/2012 | Sundar et al. |
| 8,197,444 | B1 | 6/2012 | Bazargan et al. |
| 8,208,994 | B2 | 6/2012 | Niethammer |
| 8,257,310 | B2 | 9/2012 | Donovan et al. |
| 8,295,914 | B2 | 10/2012 | Kalafut et al. |
| 8,303,547 | B2 | 11/2012 | Brown |
| 8,323,267 | B2 | 12/2012 | Haase |
| 8,328,758 | B2 | 12/2012 | Childers et al. |
| 9,320,846 | B2 | 4/2016 | Burns et al. |
| 2001/0039396 | A1 | 11/2001 | Kriesel et al. |
| 2002/0087125 | A1 | 7/2002 | Pokorney |
| 2002/0128611 | A1 | 9/2002 | Kandalaft |
| 2002/0198496 | A1 | 12/2002 | Duchon |
| 2003/0055380 | A1 | 3/2003 | Flaherty |
| 2003/0233069 | A1 | 12/2003 | Gillespie, Jr. et al. |
| 2004/0015123 | A1* | 1/2004 | Smith ............... A61D 7/00 604/65 |
| 2004/0135078 | A1 | 7/2004 | Mandro et al. |
| 2004/0138615 | A1 | 7/2004 | Lombardi |
| 2004/0143212 | A1 | 7/2004 | Trombley et al. |
| 2004/0178255 | A1 | 9/2004 | Eich et al. |
| 2004/0226183 | A1 | 11/2004 | Sielemann |
| 2005/0020983 | A1 | 1/2005 | Schreijag et al. |
| 2005/0059931 | A1 | 3/2005 | Garrison et al. |
| 2005/0165364 | A1 | 7/2005 | DiMatteo et al. |
| 2005/0277912 | A1 | 12/2005 | John |
| 2006/0178632 | A1 | 8/2006 | Trombley, III et al. |
| 2007/0060820 | A1 | 3/2007 | Lofgren et al. |
| 2007/0062250 | A1 | 3/2007 | Krulevitch et al. |
| 2007/0066939 | A1 | 3/2007 | Krulevitch et al. |
| 2007/0093752 | A1 | 4/2007 | Zhao et al. |
| 2007/0161970 | A1 | 7/2007 | Spohn et al. |
| 2008/0004507 | A1 | 1/2008 | Williams, Jr. et al. |
| 2008/0147007 | A1 | 6/2008 | Freyman et al. |
| 2008/0154187 | A1 | 6/2008 | Krulevitch et al. |
| 2008/0164970 | A1 | 7/2008 | Malzahn |
| 2008/0287865 | A1 | 11/2008 | Nielsen et al. |
| 2008/0312536 | A1 | 12/2008 | Dala-Krishna |
| 2009/0234231 | A1 | 9/2009 | Knight et al. |
| 2010/0004571 | A1 | 1/2010 | Nilsson et al. |
| 2010/0016796 | A1 | 1/2010 | Derichs |
| 2010/0114064 | A1 | 5/2010 | Kalafut et al. |
| 2010/0152675 | A1 | 6/2010 | McClintock |
| 2010/0211003 | A1 | 8/2010 | Sundar et al. |
| 2010/0274180 | A1 | 10/2010 | Donovan et al. |
| 2011/0092828 | A1 | 4/2011 | Spohn et al. |
| 2012/0024987 | A1 | 2/2012 | Naegele Nacken |
| 2012/0036937 | A1 | 2/2012 | Sprenger et al. |
| 2012/0041427 | A1 | 2/2012 | Caffey et al. |
| 2012/0116217 | A1 | 5/2012 | Lee-Sepsick et al. |
| 2012/0277661 | A1 | 11/2012 | Bernard et al. |
| 2012/0277667 | A1 | 11/2012 | Yodat et al. |
| 2012/0283186 | A1 | 11/2012 | Adams |
| 2012/0302950 | A1 | 11/2012 | Landsman et al. |
| 2012/0316460 | A1 | 12/2012 | Stout |
| 2013/0261729 | A1 | 10/2013 | Gillick et al. |
| 2014/0066860 | A1 | 3/2014 | Houfburg et al. |
| 2014/0066891 | A1 | 3/2014 | Burns et al. |
| 2014/0163339 | A1 | 6/2014 | Goldstein et al. |
| 2014/0288422 | A1 | 9/2014 | Brady et al. |
| 2015/0202361 | A1 | 7/2015 | Burns et al. |
| 2015/0202386 | A1 | 7/2015 | Brady et al. |
| 2016/0213834 | A1 | 7/2016 | Brady et al. |
| 2018/0272072 | A1 | 9/2018 | Radmer |
| 2019/0030256 | A1 | 1/2019 | Brady |

FOREIGN PATENT DOCUMENTS

| | | |
|---|---|---|
| EP | 1930603 | 6/2008 |
| JP | S62-184302 | 8/1987 |
| JP | H06-296690 | 10/1994 |
| JP | H09-506288 | 6/1997 |
| JP | 2005-523397 A | 8/2005 |
| JP | 2005-533568 A | 11/2005 |
| JP | 2007-175444 A | 7/2007 |
| WO | 84/01718 | 5/1984 |
| WO | 89/03230 | 4/1989 |
| WO | 96/11024 | 4/1996 |
| WO | 98/17974 | 4/1998 |
| WO | 02/064196 | 8/2002 |
| WO | 02/098493 | 12/2002 |
| WO | 2004/009163 | 1/2004 |
| WO | 2005/068848 | 7/2005 |
| WO | 2009/039203 | 3/2009 |
| WO | 2009/065153 | 5/2009 |
| WO | 2012/167720 | 12/2012 |
| WO | 2013/177135 | 11/2013 |
| WO | 2014/035647 | 3/2014 |
| WO | 2016/040949 | 3/2016 |

OTHER PUBLICATIONS

Cigarroa, et al., "Dosing of Contrast Material to Prevent Nephropathy in Patients with Renal Disease", Am. Jour. of Med., Jun. 1989, pp. 649-652.
Davies, Justin E. et al., "Evidence of a Dominant Backward-Propagating 'Suction' Wave Responsible for Diastolic Coronary Filling in Humans, Attenuated in Left Ventricular Hypertrophy" (Circulation. 2006;113:1768-1778).
Gurm, H. et al., "Renal-Function-Based Contrast Dosing to Define Safe Limits of Radiographic Contrast Media in Patients Undergoing Percutaneous Coronary Interventions", Journal of the American College of Cardiology, 58(9): 907-914 (2011).
PCT International Search Report and Written Opinion in International Application PCT/US2016/025671, dated Jul. 26, 2016, 16 pgs.
PCT International Search Report and Written Opinion in International Application PCT/US2013/054510, dated Dec. 4, 2013, 16 pgs.
PCT International Search Report and Written Opinion in International Application PCT/US2014/052319, dated Feb. 5, 2015, 14 pgs.
PCT International Search Report and Written Opinion in International Application PCT/US2015/021294, dated Jun. 19, 2015, 13 pgs.
PCT International Search Report and Written Opinion in International Application PCT/US2016/025302, dated Jul. 20, 2016, 13 pgs.
PCT International Search Report and Written Opinion in International Application PCT/US2018/040514, dated Sep. 12, 2018, 18 pgs.

\* cited by examiner

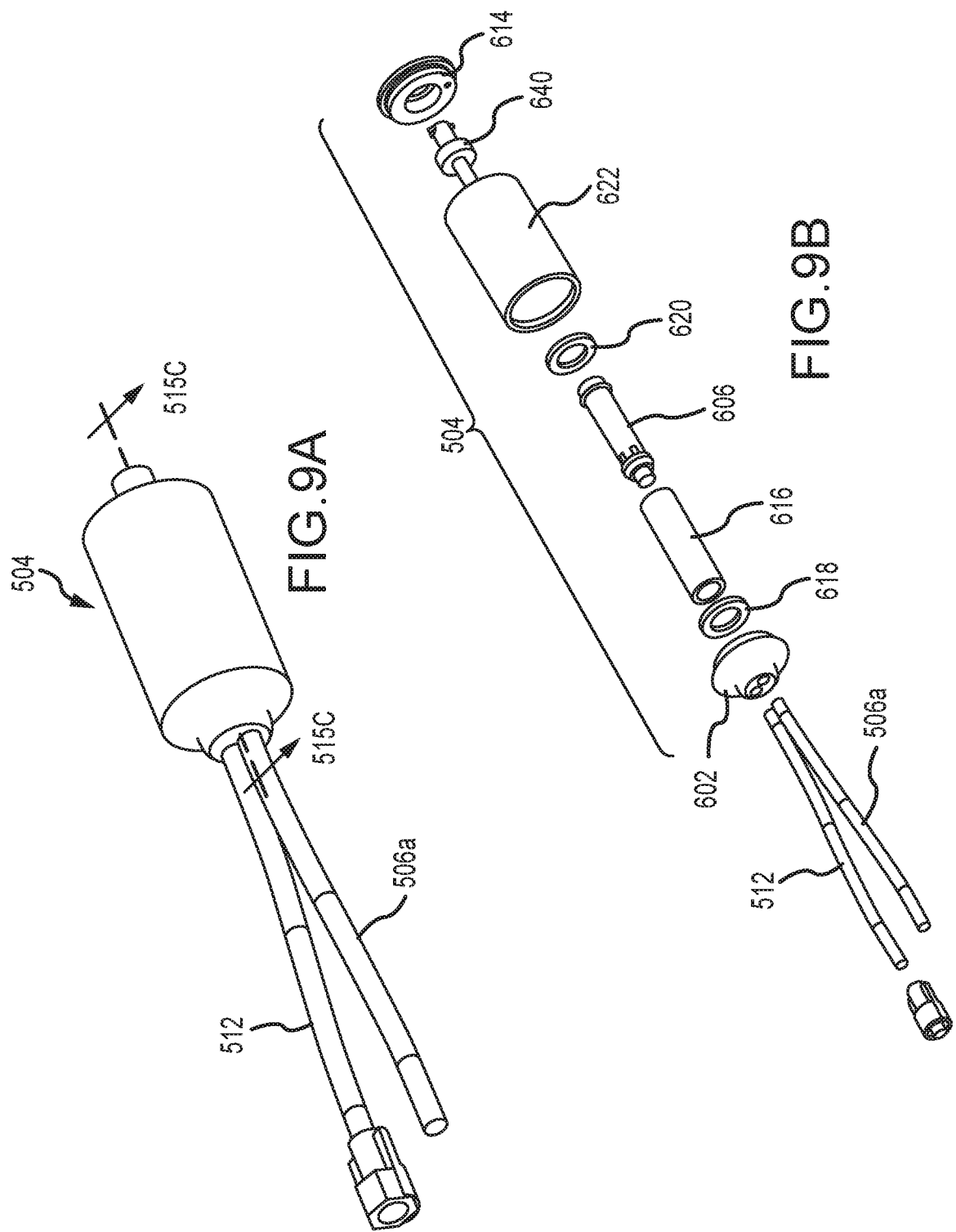

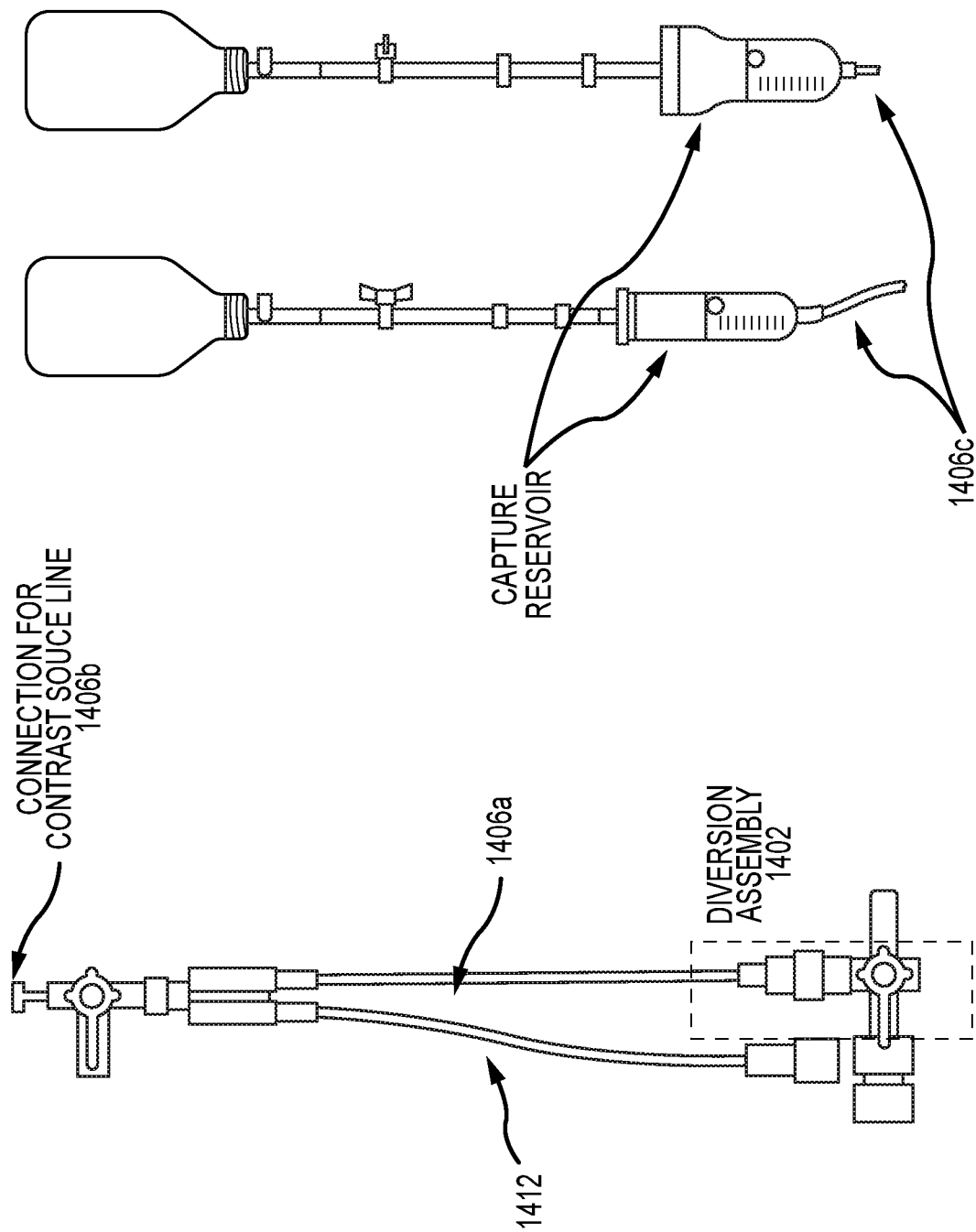

MEDIUM INJECTION DIVERSION AND MEASUREMENT

CROSS-REFERENCE TO RELATED APPLICATIONS

This application claims priority to and the benefit of U.S. Provisional Patent Application Ser. No. 62/527,919, filed Jun. 30, 2017, entitled "Contrast, Diversion, and Measurement". This application is also a continuation-in-part of U.S. patent application Ser. No. 15/089,061, filed Apr. 1, 2016, entitled "Volume Monitoring Systems"; which claims priority to and the benefit of U.S. Provisional Patent Application Ser. No. 62/141,723, filed Apr. 1, 2015, entitled "Volume Monitoring Device Utilizing Hall Sensors". U.S. patent application Ser. No. 15/089,061 is also a continuation-in-part of U.S. patent application Ser. No. 14/222,331, filed Mar. 21, 2014, entitled "Volume Monitoring Device Utilizing Light-Based Systems"; which is a continuation-in-part of U.S. patent application Ser. No. 13/975,052, filed Aug. 23, 2013, entitled "Volume Monitoring Device"; which is a continuation-in-part of U.S. patent application Ser. No. 13/839,771, filed Mar. 15, 2013, entitled "Devices and Methods for Modulating Medium Delivery"; which claims priority to and the benefit of U.S. Provisional Patent Application Ser. No. 61/694,137, filed Aug. 28, 2012, entitled "Devices and Methods for Modulating Medium Delivery". U.S. patent application Ser. No. 15/089,061 is also a continuation-in-part of U.S. patent application Ser. No. 14/851,958, filed Sep. 11, 2015, entitled "Reservoir for Collection and Reuse of Diverted Medium"; which is a continuation-in-part of U.S. patent application Ser. No. 13/839,771, filed Mar. 15, 2013, entitled "Devices and Methods for Modulating Medium Delivery"; which claims priority to and the benefit of U.S. Provisional Patent Application Ser. No. 61/694,137, filed Aug. 28, 2012, entitled "Devices and Methods for Modulating Medium Delivery". U.S. patent application Ser. No. 14/851,958 also claims priority to and the benefit of U.S. Provisional Patent Application Ser. No. 62/048,974, filed Sep. 11, 2014, entitled "Devices and Method for Modulating Medium Delivery"; and claims priority to and the benefit of U.S. Provisional Patent Application Ser. No. 62/082,260, filed Nov. 20, 2014, entitled "Devices and Methods for Modulating Medium Delivery". The disclosures of all of the above-identified applications are incorporated by reference herein in their entireties.

INTRODUCTION

This disclosure pertains to systems, devices, and methods used to control, transform or otherwise modulate the delivery of a substance, such as radiopaque contrast, to a delivery site and/or systems, devices, and methods that may be used to measure or otherwise make quantitative assessments of a medium delivered to a delivery site. More specifically, it is the intention of the following systems, devices, and methods to modulate and/or assess the delivery of media to a vessel, vascular bed, organ, and/or other corporeal structures so as optimize the delivery of media to the intended site, while reducing inadvertent or excessive introduction of the media to other vessels, vascular beds, organs, and/or other structures, including systemic introduction.

The terms medium (media), agent, substance, material, medicament, and the like, are used generically herein to describe a variety of fluidal materials that may include, at least in part, a substance used in the performance of a diagnostic, therapeutic or/and prophylactic medical procedure and such use is not intended to be limiting.

SUMMARY

This summary is provided to introduce a selection of concepts in a simplified form that are further described below in the Detailed Description. This summary is not intended to fully identify key features or essential features of the claimed subject matter, nor is it intended to describe each and every disclosed example or every implementation of the claimed subject matter, as well as is not intended to be wholly used as an aid in determining the scope of the claimed subject matter. Many other novel advantages, features, and relationships will become apparent as this description proceeds. The figures and the description that follow more particularly exemplify illustrative examples.

In one aspect, the technology relates to a system for measurement automation of a fluid injected into a patient with a fluid injection apparatus, the system including a reservoir; the fluid injection apparatus including: a delivery conduit for insertion into the patient and delivery of the fluid into the patient; an injector for injecting the fluid into the patient via an injection fluid path fluidly coupling the injector to the delivery conduit; a diverter assembly disposed between the delivery conduit and the injector, said diverter assembly configured to divert at least a portion of the fluid away from an injection fluid path between the injector and the delivery conduit, the diverter assembly being fluidly coupled to the reservoir, wherein the diverter assembly is configured to allow at least the portion of the fluid injected by the injector to be simultaneously diverted away from the delivery conduit based on at least one of a pressure and a flow of the injection fluid path, wherein the diverted fluid is stored in the reservoir for reuse; and a connector fluidly coupling the injector to the diverter assembly and the delivery conduit; and a measurement automation apparatus including: an injector sensor module configured to be applied to a plunger and a housing of the injector, the injector sensing module is configured to generate data for the determination of a volume displacement within the injector; a reservoir sensor module configured to be applied to a plunger and a housing of the reservoir, the reservoir sensor module configured to generate data for the determination of a volume displacement within the reservoir; a processor configured to receive the data from the injector sensor module and the reservoir sensor module to determine the amount of the fluid delivered to the patient based at least in part on the data; and a display operatively coupled to the processor for displaying the amount of fluid delivered to the patient.

In an example of the above aspect, the injector sensor module includes a hall sensor disposed on the plunger of the injector and a magnet disposed on the housing of the injector. In another example, the reservoir sensor module includes a hall sensor disposed on the plunger of the reservoir and a magnet disposed on the housing of the reservoir. In yet another example, the plunger of the reservoir is biased towards a fluid inlet of the reservoir. In still another example, at least one of the injector sensor module and the reservoir sensor module includes a light sensor module.

In another example of the system further includes a manifold coupled to the injection fluid path, wherein the manifold includes at least one actuatable valve. In another example, the system further includes a contrast return line fluidly coupling the reservoir and the at least one actuatable valve. In yet another example, the system includes a position sensor associated with the contrast return line, said position sensor being a pressure sensor. In still another example, the system includes a position sensor associated with the at least one actuatable valve. In certain examples, the system includes a second actuatable valve fluidly coupling a saline source to the manifold. In examples, the system includes a position sensor associated with the second actuatable valve. In some examples, the system includes a position sensor associated with the at least second saline source conduit, wherein the position sensor includes a pressure sensor. In other examples, the measurement automation apparatus is configured to disregard the data generated by at least one of the injector sensor module and the reservoir sensor module based at least in part on a signal sent from the position sensor.

In another aspect, the technology relates to a method of monitoring an injection of a fluid via a delivery conduit into a patient, the method including: receiving a continuous injection signal from an injection sensor associated with an injection device, wherein the injection device is configured to inject the fluid into the fluid conduit; receiving a continuous reservoir pressure signal from a reservoir pressure sensor associated with a reservoir, wherein the reservoir is configured to receive the fluid from the delivery conduit, via a diversion conduit; and calculating automatically and continuously a volume of the fluid injected to the patient based at least in part on the continuous injection signal and the continuous reservoir pressure signal.

In an example of the above aspect, the method includes receiving a continuous diversion signal from a diversion sensor associated with a diversion valve, wherein the diversion valve is configured to selectively engage the diversion conduit with the delivery conduit; and wherein calculating automatically and continuously the volume of the fluid injected to the patient is further based at least in part on the continuous diversion signal. In another example, the method includes receiving a flush signal from a flush valve position sensor associated with a flush valve, wherein the flush valve is configured to selectively engage a flush liquid source with the fluid conduit. In yet another example, calculating automatically and continuously the volume of the fluid injected to the patient is further based at least in part on the flush signal. In another example, the method includes suspending the automatic and continuous calculation of the volume of the fluid injected to the patient upon receipt of the flush signal. In still another example the method includes displaying the volume of the fluid injected to the patient.

In another example of the above aspect, the reservoir pressure sensor is a hall sensor module. In another example, the diversion sensor is a stopcock position sensor. In yet another example, the injection sensor includes a hall sensor module having a hall sensor disposed on a first portion of the injection device and magnet disposed on a second portion of the injection device. In still another example, the flush valve position sensor includes an on/off sensor.

Further, in another aspect, the technology relates to a system for modulating a fluid being delivered to a patient and the ability to measure the amount actually delivered to the patient site. A myriad of ways of measuring a volume in a chamber, and the subsequent amount of medium actually injected to a site in a patient, are described. Further, the ability to modulate the delivery of a medium to a patient is exemplarily described. The modulation in one aspect may include diversion of a portion of medium being injected by a syringe (or the like, such as an automated pump injector). An aspect of the technology relates to measurement of a total amount of medium ejected from a syringe/chamber, while measuring an amount of medium diverted away from the patient into a "diversion" reservoir, so as to determine the actual volume delivered to an intended site in the patient. Further, some examples may exemplarily describe means and methods that may further accommodate media (such as saline) injected by the injector (or the like, such as a syringe) that is not intended to be measured as being delivered to the patient site In another aspect, the technology relates to methods and systems for determining an amount of medium injected into a patient, the method including: receiving an injection signal from a sensor associated with an injection syringe; receiving a diversion signal from a sensor associated with a diversion reservoir; and determining the amount of medium injected based at least in part on the injection signal and the diversion signal. In an example, methods and/or systems include or are configured to send a signal associated with the amount of medium injected. In another example, the methods and/or systems include or are configured to display the amount of medium injected. In yet another example, the methods and or systems include or are configured to receive a flush signal associated with a valve of a saline flush system. In still another example, the methods and/or systems include or are configured to disregard at least one of the injection signal and the diversion signal based at least in part on the flush signal. In another example, the methods and/or systems include or are configured to adjust a position of at least one valve based at least in part on the flush signal.

BRIEF DESCRIPTION OF THE DRAWINGS

There are shown in the drawings, embodiments which are presently preferred, it being understood, however, that the technology is not limited to the precise arrangements and instrumentalities shown.

FIG. 9A is a perspective view of another example of a medium diversion reservoir.

FIG. 9B is a perspective exploded view of the medium diversion reservoir of FIG. 9A.

FIG. 15 depicts a diversion assembly.

FIG. 16 depicts examples of commercially available reservoirs for capturing contrast.

DETAILED DESCRIPTION

Figure 1:
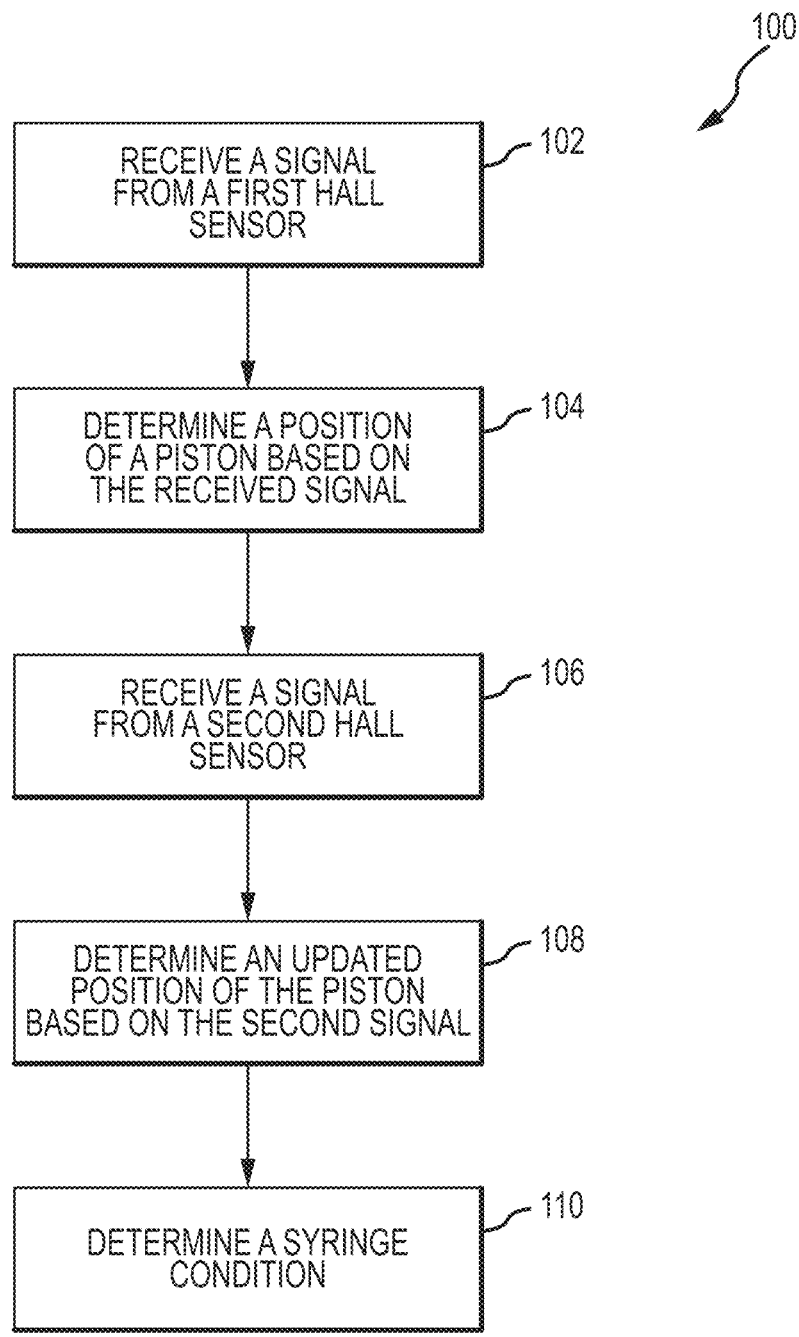
FIG. 1 depicts a method of using an injector monitoring device.

There are numerous occasions in the diagnostic, prophylactic and treatment practice of medicine wherein an agent, medicant, or medium is preferably delivered to a specific site within the body, as opposed to a more general, systemic introduction. One such exemplary occasion is the delivery of contrast media to coronary vasculature in the diagnosis (i.e., angiography) and treatment (i.e., balloon angioplasty and stenting) of coronary vascular disease. The description, as well as the devices and methods described herein, may be used in modulating and/or monitoring medium delivery to the coronary vasculature in prevention of toxic systemic effects of such an agent. One skilled in the art, however, would recognize that there are many other applications wherein the controlled delivery and/or quantitative assessment of a media to a specific vessel, structure, organ or site of the body may also benefit from the devices and methods disclosed herein. For simplicity, these devices and methods may be described as they relate to contrast media delivery modulation and/or measurement. As such, they may be used in the prevention of Contrast Induced Nephropathy; however, it is not intended, nor should it be construed, so as to limit the use to this sole purpose. Exemplary other uses may include the delivery, injection, modulation, or measurement of: cancer treatment agent to a tumor, thrombolytic to an occluded artery, occluding or sclerosing agent to a vascular malformation or diseased tissue; genetic agent to a muscular bed, neural cavity or organ, emulsion to the eye, bulking agent to musculature and/or sphincter, imaging agent to the lymphatic system, antibiotics to an infected tissue, supplements in the dialysis of the kidney, to name but a few.

Contrast Induced Nephropathy (CIN) is a form of kidney damage caused by the toxic effects of dyes (radiopaque contrast media) used, for example, by cardiologists to image the heart and its blood vessels during commonly performed heart procedures, such as angiography, angioplasty, and stenting. In general, the dye is toxic and is known to damage kidneys. Although most healthy patients tolerate some amount of the "toxicity," patients with poorly or non-functioning kidneys may suffer from rapidly declining health, poor quality of life, and significantly shortened life expectancy. Potential consequences of CIN include: irreversible damage to the kidneys, longer hospital stays, increased risk of heart disease, increased risk of long-term dialysis, and ultimately, a higher mortality risk. For patients who acquire CIN, their risk of dying remains higher than others without CIN, and this risk can continue up to five years after their procedure. CIN has a significant economic burden on the healthcare system and currently there is no treatment available to reverse damage to the kidneys or improper kidney performance, once a patient develops CIN.

To date, there have been attempts in reducing the toxic effects of contrast media on patients who undergo procedures involving dyes, especially those patients who are at high risk for developing CIN. Some of these efforts have been to: change the inherent toxicity (of a chemical or molecular nature) of the dyes, reduce the total amount of contrast agent injected (through injection management and/or dye concentration), and remove media through coronary vasculature isolation and blood/contrast agent collection systems, to name a few. These methods and devices used in the control of the toxic effects of contrast agents have had their inherent compromises in effectively delivering a contrast media specifically to a target site while minimizing the systemic effects. As an example, changing the composition of a dye and/or injection concentration may help reduce a contrast agent's inherent toxicity at the expense of the contrast agent's ability to perform its intended function (e.g., visualization of vasculature).

Conversely, the ability to "collect" contrast agent laden blood "downstream" from the visualization site may ensure visualization, but requires the complexity of placement and operation of a collection system.

Other attempts to manage the amount of contrast agent delivered to a patient have employed automated, powered (versus manual, syringe-injected) contrast media injection systems. Close monitoring and control of the total quantity of contrast agent injected may have a positive impact in reducing the incidence of CIN. However, these injection systems are expensive (including capital equipment and disposables), cumbersome to use within a cath lab, and take additional time and expertise to set up and operate properly. Improper use could negate any benefits seen by better management of the quantity of the contrast agent delivered to a patient, and the additional time required to set up such a system may also add significant complexity to a procedure. The devices and methods described herein may measure or otherwise quantitatively assess the amount of medium injected or delivered to a delivery site using a relatively fast, simple, economical, and safe system.

Figure 13:
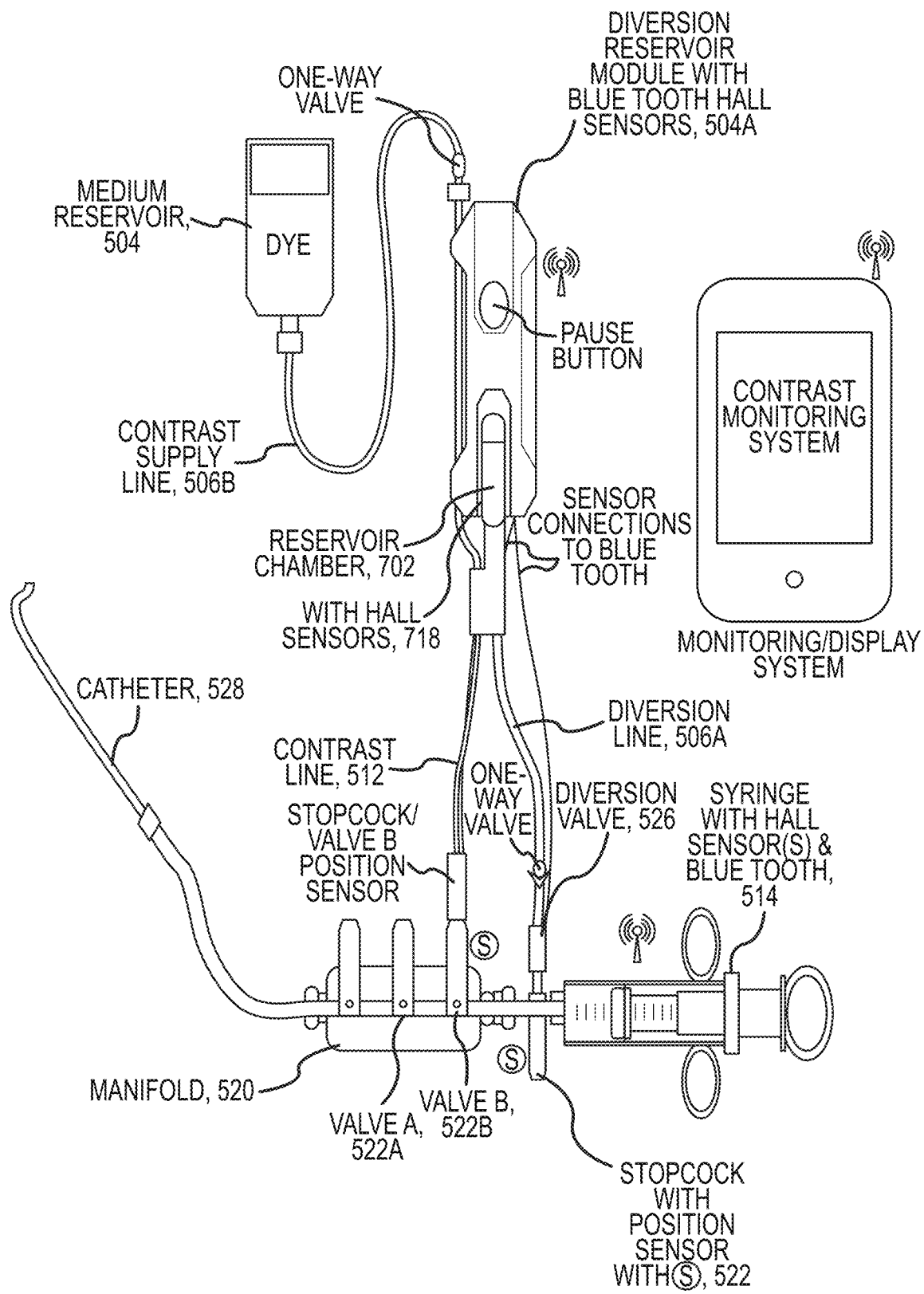
FIG. 13 graphically illustrates a medium management system with a diversion reservoir.

The measurement systems described herein may be employed as a system of quantitative assessment or in combination with a modulator. Additional systems are described in U.S. patent application Ser. Nos. 14/851,958 and 15/089,061, the disclosures of which are hereby incorporated by reference herein in its entirety. An exemplary embodiment may be found in FIG. 13, depicting a modulator and a reuse diversion reservoir wherein the system may be constructed so as to measure the amount of an agent delivered from the system to the patient while also employing a diversion reservoir to reuse the portion of medium injected through the diversion of a portion of the injected medium. Conversely, FIG. 14, for example, describes the use of a measurement system for the quantitative assessment of a volume of medium delivered and the inherent analysis of the total volume delivered to the patient versus some predetermined critical amount, such as the Gurm ratio, whether or not it is used with a modulator and a diversion reservoir (for contrast reuse). It should be understood that measurements may be performed prior to a medium being modulated, simultaneously with modulation, or after the modulation process, if desired. Further, it is also contemplated that the measurement devices and methods may be used with any of the modulation systems, such as described in U.S. patent application Ser. Nos. 13/839,771 and/or 14/851,958. Moreover, the embodiments described herein are exemplary in nature and should not be construed as limiting the various combinations possible.

Some embodiments of control and modulation devices disclosed herein may send and/or receive a sensor signal so as to coordinate a valving, controlling, or otherwise modulating function on an injection agent before the agent enters an intended target injection site. Modulation may include, for example, valving (or otherwise modulating) an injection dispensed from an injection device. As described in U.S. patent application Ser. Nos. 13/839,771 and/or 14/851,958, indirect valving (or otherwise controlling mechanisms) may be proximally or distally positioned within, about, and/or upon the agent delivery system. Moreover, embodiments herein may describe different systems and methods, or combinations thereof, to address user preferences. For example, a user may simply want to measure the medium injected by a syringe (which may include total volume injection) to a patient. Such as system might be simpler than an alternative configuration wherein the user wants to measure a medium injection when the system involves a diversion (modulation) function.

In addition, end users may have varied different needs, and as such, the various components and methods described herein for measurement, modulation, and diversion (i.e., for example, a reservoir for reuse of the medium) may be used in part, or whole, to address these needs. As an example, one user may only want to measure an injection (while not measuring a saline flush); another user may want to employ a modulator and measurement, while not capturing the diverted medium for reuse (medium wasted); further, another user may want to employ measurement and a reservoir for reuse, but would prefer to use their existing system for reuse capture. These are merely a small list of the various needs addressed by combining different components of the described embodiments herein, and they should be viewed as exemplary and not limiting. Further, the use of an injector has been described and as such it could be a syringe and/or a power injector (e.g., Acist CVi Injector). Construction of embodiments described herein may vary depending on the injector; however, the principals of the embodiments may remain the same.

The embodiments described herein may include various elements or components to measure and/or detect a displacement of a plunger within a chamber, such as a syringe. And, with the detection of a positional relationship of a plunger within a chamber, a user may explicitly or implicitly determine a volume of media that may have been ejected from a chamber. Some of the embodiments described may include various sources in the generation of light, as well as components to detect or sense the light, depending on the positional relationship of the plunger/piston and the chamber. Linear encoders, inductive sensors, capacitive touch sensors (with metal actuator in plunger), ultrasonic emitters/receivers, pressure sensors, optical encoders (with fine pitch slots and light source), strain gauges (i.e., to measure weight), electromagnetic emitters/receivers (e.g., navigational systems) are alternative technologies contemplated for the use of measuring an injection delivered from an injector to a patient, with or without measuring a "diversion" reservoir. Other alternative embodiments capable of identifying positional relationships of a plunger and chamber (and changes thereof) may include, without limitation, the following technologies. A Hall sensor (coiled wire along syringe axis) may be placed on, or in proximity to, the chamber with a magnet attached to the plunger (so as to act as a variable proximity sensor). Multiple low sensitivity Hall sensors may be disposed along the chamber of the syringe with a magnet attached to the plunger. Still other embodiments of systems utilizing multiple Hall sensors are described herein. Laser light may be emitted and detected to determine a positional relationship of the plunger along the chamber axis. An absolute encoder may be used to "read" the direct displacement of the plunger. Many of these systems described herein include at least a two part, or portion, of a sensing system One part may be used to send or cause the creation of a signal (or change), and the second part may be used to read, sense, or measure a difference in a signal (or change). Typically, in the many of the embodiments described herein, one of the components (i.e., part, portion, etc.) of measurement may be associated, attached to, or in the proximity with the plunger of an injector; whereas, the at least second part (i.e., component, portion, etc.) may be attached to, associated with, or in the proximity of the injector housing. One example of this may be found in FIG. 4, components 350a and 350b.

Figure 3:
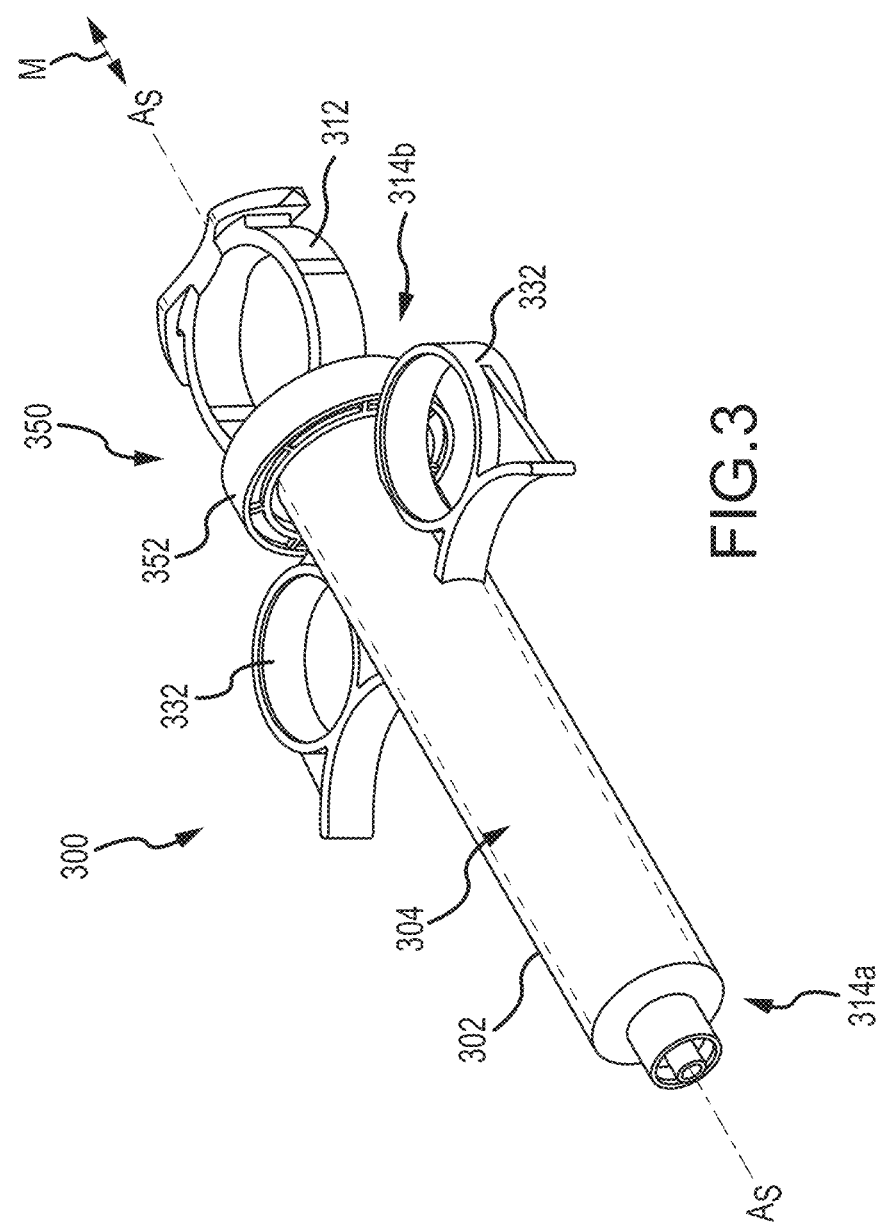
FIG. 3 depicts a perspective view of a first embodiment of a monitoring syringe utilizing a Hall sensor module.

FIG. 3 depicts a perspective view of an embodiment of a monitoring syringe 300 utilizing a Hall sensor module, which is described in more detail below. The monitoring syringe 300 includes a syringe housing 302 defining an inner bore 304. A plunger or piston, which is described in more detail below, is slidably received in the bore 304. More specifically, the piston is slidably engaged with an interior surface of the bore 304 and linear movement M of a plunger shaft within the bore 304 moves the piston. Movement M is along the syringe axis As. A thumb ring 312 may be utilized to push and pull the plunger along axis As, as described in more detail below. As the plunger is moved Min a direction towards the discharge end 314a of the syringe housing 302, the fluid (e.g., media) contained therein is discharged into a tube or needle (not shown) and delivered to a patient. Two finger rings or tabs 332 receive the fingers of a user during use. Note that throughout the description a cylindrical-type housing 302 and inner bore 304 are described; however, it is contemplated that there may be a variety of constructions of a housing/bore 302/1204 and plunger that provide the function as anticipated herein and the shape (including rectangular, ovular, triangular cross-section, etc.), in and of itself, should not be limiting. The monitoring syringe 300 also includes a Hall sensor module 350, described in more detail below. One component of the Hall sensor module 350 is a magnet retention ring 352, which is disposed on an outer or exterior surface of the syringe housing 302. In the depicted embodiment, the magnetic retention ring 352 is disposed proximate a proximal end 314b of the housing 302, but it may be disposed in other locations along the housing 302.

Figure 4:
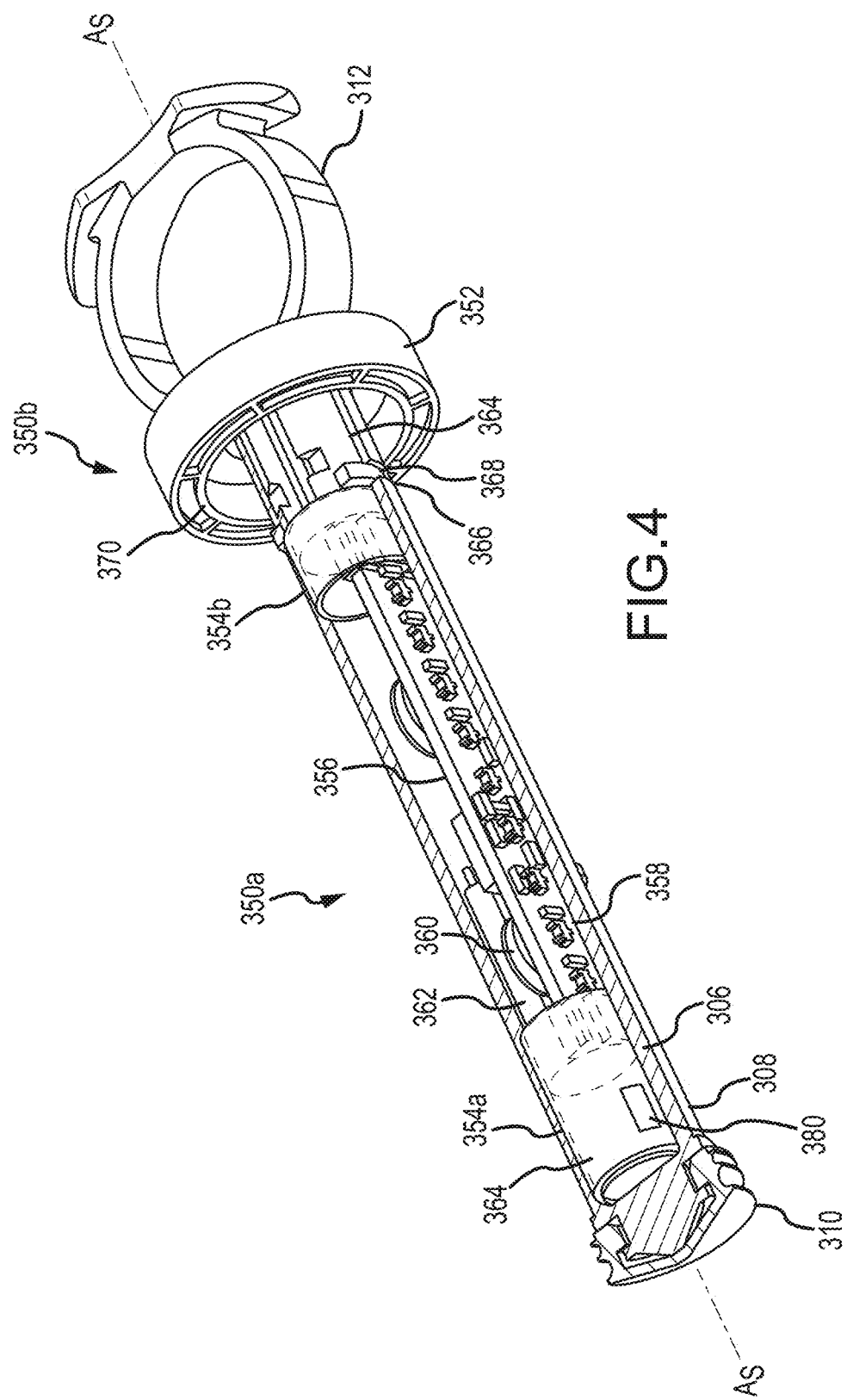
FIG. 4 depicts a partial perspective sectional view of the monitoring syringe of FIG. 3, depicting the Hall sensor module.

FIG. 4 depicts a partial perspective sectional view of the monitoring syringe 300 of FIG. 3, depicting the Hall sensor module 350. Certain components 350a of the Hall sensor module 350 are disposed within an inner chamber of a hollow shaft 308 of the plunger 306, while certain components 350b are disposed on an exterior surface of the syringe housing. These various components 350a, 350b are described in more detail below. So-called internal components 350a (i.e., internal to the plunger 306) include retention inserts 354a, 354b, a base or circuit board 356, and a plurality of Hall sensors 358 disposed thereon. One or more batteries 360 and a control switch 362 may also be secured to the circuit board 356. Signals from the Hall sensors 358 may be first processed by the circuit board 356, which may determine the position of the plunger 306, the volume of media in the syringe, etc., and then send this information to an associated system via the transmitter 380 for further analysis, display to a doctor, etc. In another embodiment, e.g., if a non-processing base 356 is used, the signals from each Hall sensor 358 may be sent directly via the transmitter 380 to an associated system for processing.

The distal retention insert 354a may be inserted into the shaft 308 so as to be near the piston 310. The distal retention insert 354a may define a void 364, which may contain a wireless transmitter 380, such as a Bluetooth transmitter. The transmitter 380 may send signals from the Hall sensors 358 to an associated signal processing device such as described herein. In an alternative embodiment, a cable connection such as described above, may be utilized. The proximal retention insert 354b is disposed in the hollow shaft 308 near the thumb ring 312. Together, the distal retention insert 354a and the proximal retention insert 354b support, protect, and retain the circuit board 356 within the hollow shaft 308. These two components may be configured for a snug fit in the shaft 308, or may include a key or other projection to engage with an opening or slot in the shaft 308, so as to prevent rotation. The retention inserts 354a, 354b may be permanently fixed within the shaft 308, although configuring the inserts 354a, 354b for removal may be advantageous so as to allow for replacement or repair of the circuit board 356, batteries 360, etc. In one embodiment, the thumb ring 312 may include a resilient base 364 including a plurality of projections 366 that may be engageable with mating slots 368 in the shaft 308. Disengaging these projections 366 allows for removal of the retention inserts 354a, 354b and other internal components. A plurality of Hall sensors 358 are depicted. A greater or fewer number of sensors 358 may be utilized in various embodiments, although a greater number of sensors 358 may provide for more accurate determinations with regard the position of the plunger 306. The Hall sensors 358 are disposed linearly within the chamber so as to be substantially aligned with, or parallel to, the axis As.

External components 350b include the magnet retention ring 352, which holds a plurality of magnets 370, which may be arc magnets, in the depicted embodiment. In other embodiments, cube, cylindrical, or other magnets may be utilized. The positions of the magnets 370 are fixed relative to and about the syringe housing. The arc magnets 370 form a substantially circular magnetic field through which the shaft 308 (and the Hall sensors 358) pass when the shaft 308 is withdrawn from or inserted into the inner bore of the syringe. The circular magnetic field enables the Hall sensors 358 to detect the field, regardless of the rotational position of the plunger 306 about the axis As. In other embodiments, the magnets 370 may be secured directly to the syringe housing without the magnet retention ring.

Figure 5:
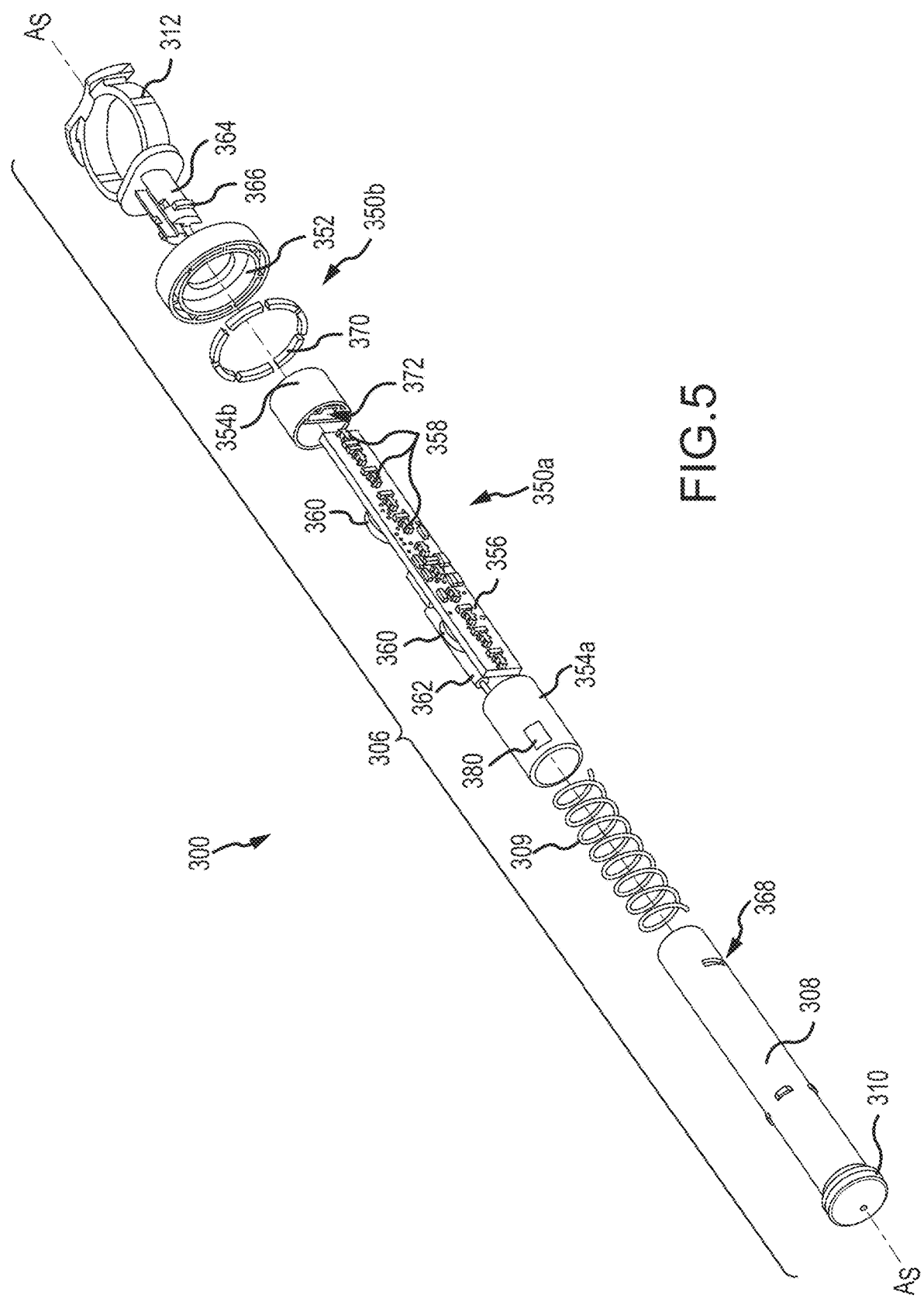
FIG. 5 depicts a partial exploded perspective view of the monitoring syringe of FIG. 4.
Figure 6:
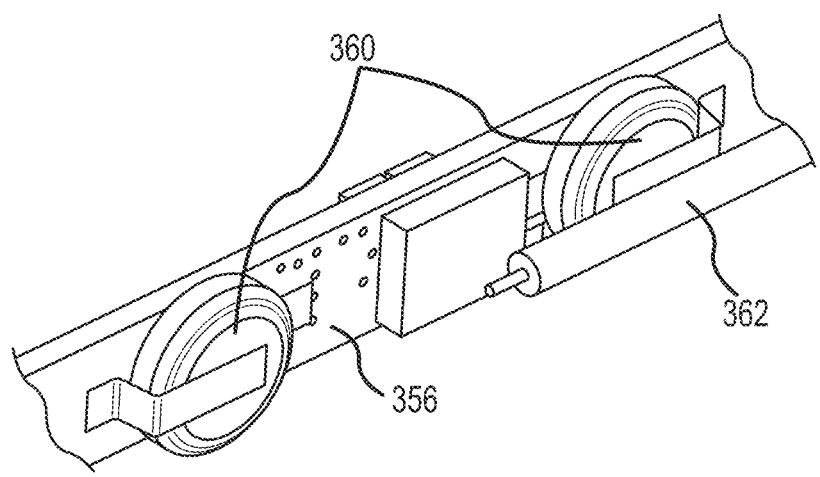
FIG. 6 depicts a partial perspective view of a Hall sensor module.

FIG. 5 depicts a partial exploded perspective view of a portion of the monitoring syringe 300, as seen in FIG. 4. More specifically, the plunger 306, Hall sensor module internal components 350a, and Hall sensor module external components 350b are depicted. In general, certain of these components are described above in FIGS. 3-4 and are not necessarily described further. In the depicted embodiment, however, both the distal retention insert 354a and proximal retention insert 354b include shaped recesses 372 that are configured to receive the circuit board 356 so as to hold that element in place. The recesses 372 are disposed in the inserts 354a, 354b so as to conserve space within the hollow shaft 308 of the plunger 306. On a side of the circuit board 356 opposite the Hall sensors 358 are disposed a plurality of batteries 360. This is also depicted in FIG. 6. Additionally, a switch 362 may be disposed proximate the batteries 360 or elsewhere within the hollow shaft 308. The switch 362, in certain embodiments, may be a reed switch that detects plunger movement and moves to an engaged or activated position. The switch 362 is not required but may help preserve power when the syringe 300 is not in use.

When activated, the switch 362 selectively connects power from the batteries 360 to either or both of the plurality of Hall sensors 358 and the wireless transmitter 380. In other embodiments, a manually-operated switched, such as a pull tab, button, or rocker switch may be actuated by the user.

In a further embodiment of a system, the measurement components of a monitoring syringe 300 could also be utilized to measure a volume of medium diverted by a modulator to a medium diversion reservoir, in systems that employ a reservoir in the introduction of contrast to a patient. Such medium diversion reservoirs, and their incorporation into related medium management and monitoring systems, are described elsewhere herein. In such cases, the inner bone 304 may form a fluid reservoir to capture medium that may diverted by a modulator away from the injection of medium to the delivery catheter. In an additional embodiment of a reservoir, the chamber may be sufficiently pressurized by a force acting upon the plunger 306 to facilitate controlled filling, release and measurement of a medium within the chamber. The force may bias the piston 310 into the fluid contained in the bore 304, while the Hall sensors 358 continue to detect a position of the plunger 306. As in the depicted example of FIG. 5, to configure the monitoring syringe 300 as a pressurized diversion reservoir, a spring 309 may be disposed about the hollow shaft 308 of the plunger 306. This spring 309 biases the piston 310 towards the discharge end 314a of the syringe housing 302. Other spring configurations and/or biasing mechanisms may be utilized, wherein they may be generally disposed about the syringe axis As so as to provide for a balanced application of force.

Figure 7:
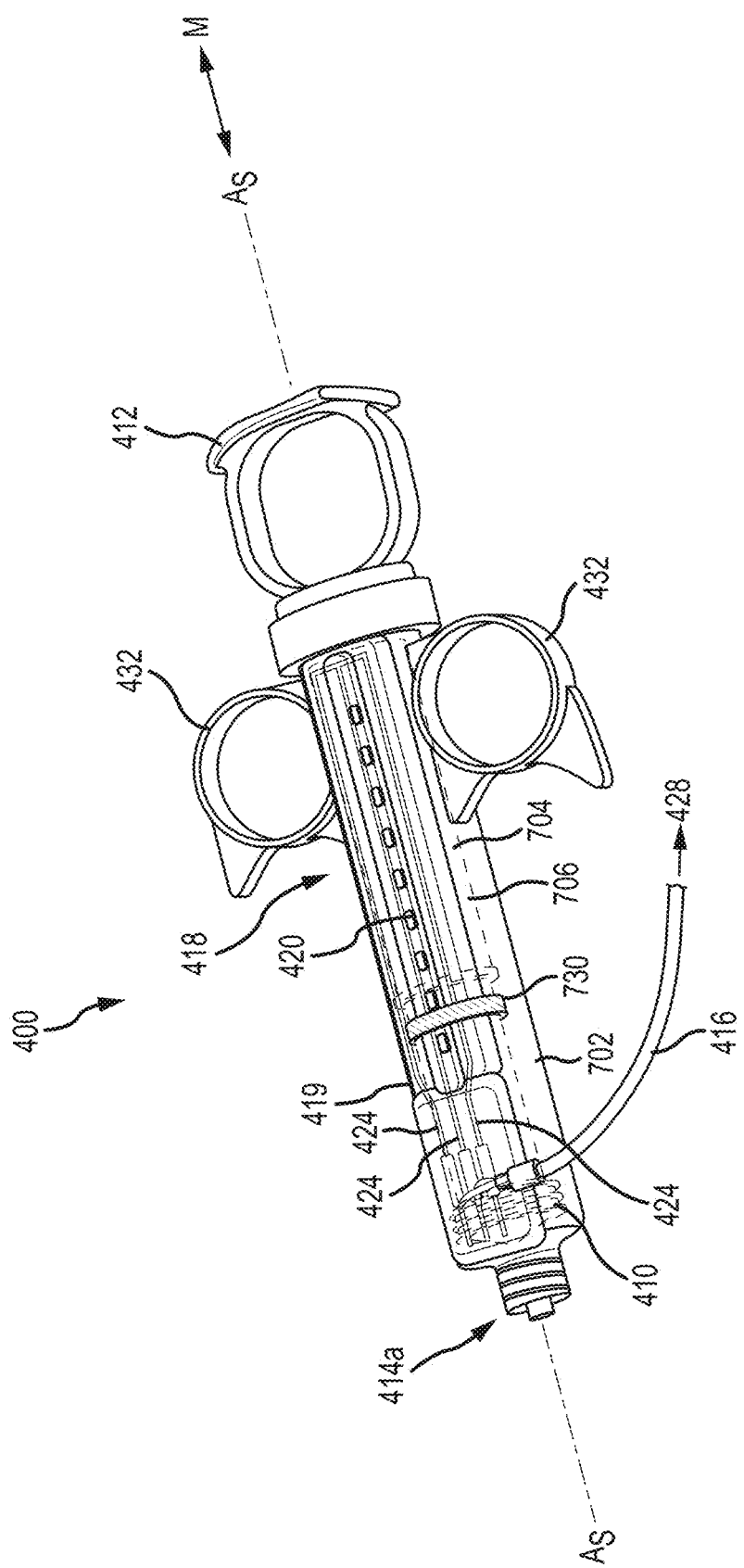
FIG. 7 depicts a perspective view of a second embodiment of a monitoring syringe utilizing a Hall sensor module.

FIG. 7 depicts a perspective view of a second embodiment of a monitoring syringe 400 utilizing a Hall sensor module. The monitoring syringe 400 includes a syringe housing 402 defining a hollow inner bore. A plunger 406 including a shaft 408 and a piston 410 is slidably received in the bore. More specifically, the piston 410 may be slidably engaged with an interior surface of the bore and linear movement M of the shaft 408, within the bore, moves the piston 410. Movement M is along the syringe axis As. The plunger 406 is moved back and forth within the bore 404 by the movement of a thumb pad, such as a thumb-ring 412. As the plunger 406 is moved M in a direction towards the discharge end 414a of the syringe housing 402, the fluid contained therein is discharged into a manifold assembly, tube, or needle (not shown) and delivered to a patient.

As an alternative embodiment to that depicted in FIGS. 4-5, a Hall sensor module 418 may be secured to an exterior surface of the syringe housing 402, rather than securement to the plunger. The Hall sensor module 418 includes a Hall sensor housing 419 that encloses a plurality of Hall sensors 420. As described above with regard to FIGS. 3-5, a greater number of discrete Hall sensor elements may improve accuracy. One or more leads or wires 424 extend from an end of the Hall sensor module 418. A cable 416 connects at an end 428 to an interface unit that analyzes the output of the Hall sensor module 418 and provides this information to a user of the monitoring syringe 400, typically on a display. In other embodiments, communication may be via a radio, Bluetooth, of other wireless connection, as described herein. The displayed information may include volume of the chamber, volume remaining, volume dispensed, fluid type, flow rate, fluid pressure or temperature and/or other information, as required or desired for a particular application. As described above, the signals from the Hall sensors may first be processed by an associated circuit board then sent to an interface unit, or the discrete signals may be sent to the interface unit for processing.

In the depicted embodiment, the shaft 408 of the plunger 406 has one or more magnets 430 disposed thereon or within the shaft 408. The magnet 430, in this case, includes a plurality of arc magnets disposed about the shaft 408. As the plunger 406 is slidingly moved M along the axis As, the magnet 430 passes in front of the Hall sensors 420 of the Hall sensor module 418. The magnetic field generated by the magnet 430 is detected by the Hall sensor 420. The Hall sensor 420 sends a signal to the interface unit that determines the position of the plunger 406 within the syringe housing 402, based on the position of the magnet 430 as detected by an individual Hall sensor 420. Thus, the position of the plunger 406 can be determined. The interface may also determine the various types of information listed above, based on a known diameter and length of the bore 404 of the syringe housing 402. Two finger rings or tabs 432 receive the fingers of a user during use. A stop 434 prevents the plunger 406 from being pulled out of the syringe housing 402.

Although the embodiments depicted in FIGS. 3-7 depict a plurality of Hall sensors, other embodiments of monitoring syringes may utilize one or more sensors of various types. For example, a single sensor, or multiple sensors, may be used to measure a magnetic field, material resistance, capacitance, etc. The measurements from such sensors may be utilized to determine the linear position of the plunger within the syringe. Examples of such sensors include, but not limited to, Hall effect sensors (as described in more detail herein), inductive sensors, capacitive touch sensors, and others.

FIG. 1 depicts a method 100 of using a monitoring syringe utilizing Hall sensors. At operation 102, a signal is received from a first Hall sensor, the position of which in a plunger shaft is known, relative to other Hall sensors in the shaft. Based on the position of the first Hall sensor and the signal received from said sensor, a position of a piston is then determined in operation 104. Since a cross-sectional area, diameter, or other dimension of the syringe is known, the amount of media in the syringe based on the position of the piston can be determined. In embodiments where multiple Hall sensors are used, a signal may be received from a second Hall light sensor having known characteristics (e.g., position) in operation 106. An updated position of the piston may then be determined based on the received signal from the second Hall sensor and the signal in operation 108. At any time a signal is received from a known Hall sensor, a condition of the syringe (such as those described herein) may be determined, as in operation 110. As described above, the method 100 may be performed on the circuit board within the monitoring syringe, then sent to an associated system via the transmitter for further analysis or display to a surgeon, etc. In an alternative embodiment, each signal may be sent via the transmitter to an associated system for processing, analysis, display, etc.

In addition, the methods described in FIG. 1, when used in a system employing a diversion reservoir, may further incorporate a measurement determined in a chamber collecting medium diverted from an injection (i.e., through a modulator). Having a total amount of medium injected by the syringe (as determined by a sensing apparatus), minus the amount of medium diverted (as determined by a sensing apparatus), provides the total amount of the injection actually delivered to the patient.

Figure 2:
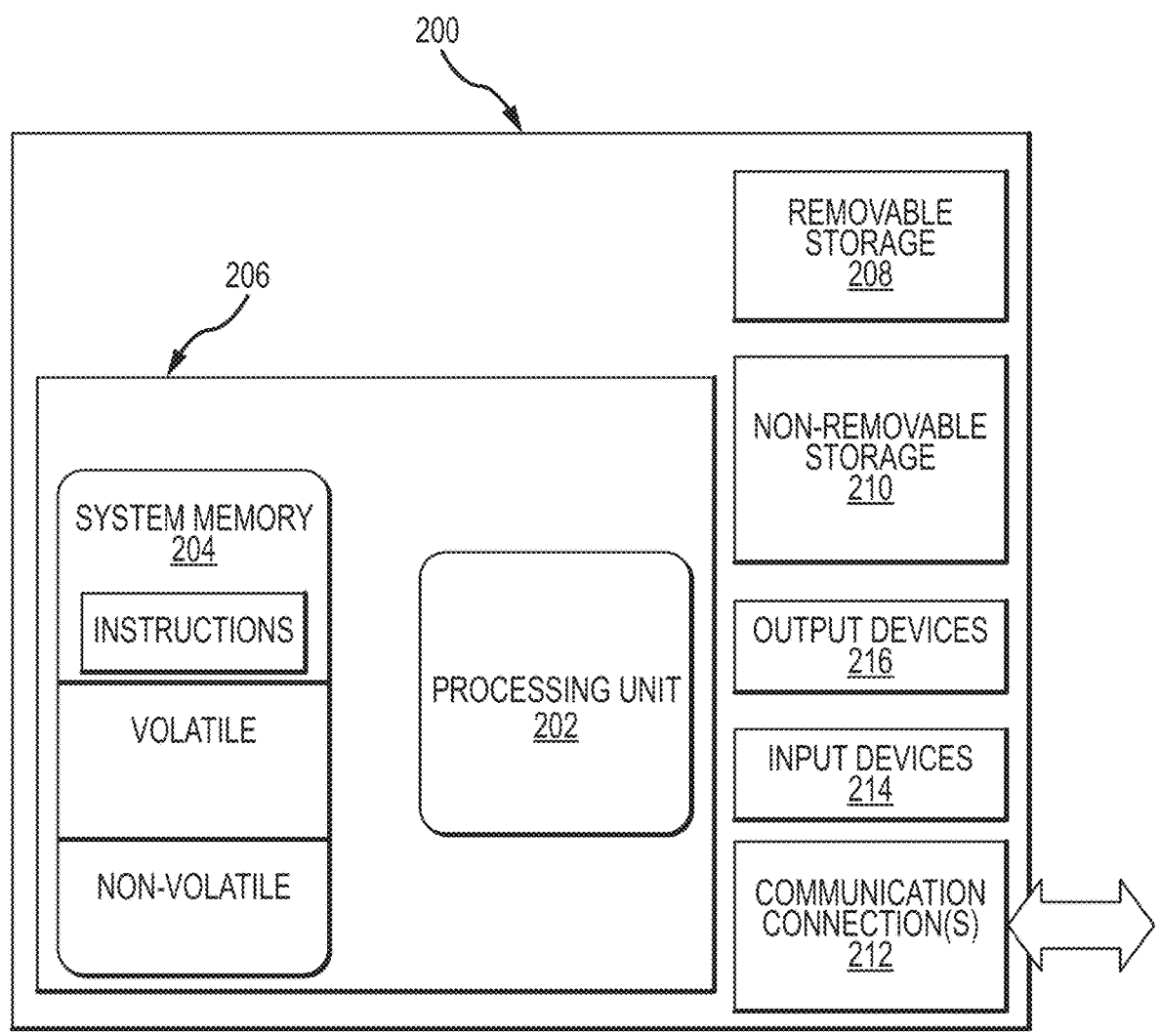
FIG. 2 depicts one example of a suitable operating environment in which one or more of the present examples may be implemented.

FIG. 2 illustrates one example of a suitable operating environment 200 in which one or more of the present embodiments may be implemented. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 200 may typically include at least one processing unit 202 and memory 204. Depending on the exact configuration and type of computing device, memory 204 (storing, among other things, instructions to perform the monitoring methods described herein) may be volatile (such as RAM), non-volatile (such as ROM, flash memory, etc.), or some combination of the two. This most basic configuration is illustrated in FIG. 2 by line 206. Further, environment 200 may also include storage devices (removable, 208, and/or non-removable, 210) including, but not limited to, magnetic or optical disks or tape. Similarly, environment 200 may also have input device(s) 214 such as touch screens, keyboard, mouse, pen, voice input, etc. and/or output device(s) 216 such as a display, speakers, printer, etc. Also included in the environment may be one or more communication connections, 212, such as LAN, WAN, point to point, Bluetooth, RF, etc.

Operating environment 200 may typically include at least some form of computer readable media. Computer readable media can be any available media that can be accessed by processing unit 202 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 200 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet. In some embodiments, the components described herein comprise such modules or instructions executable by computer system 200 that may be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 200 is part of a network that stores data in remote storage media for use by the computer system 200.

The monitoring injectors such as those described above may be utilized in various types of medium management systems to control and monitor medium injection into patients. Two exemplary medium management systems, as well as components thereof, are described below in the following figures. These are but two types of systems that may benefit from the monitoring technologies described herein. Other systems and configurations thereof will be apparent to a person of skill in the art.

Figure 8:
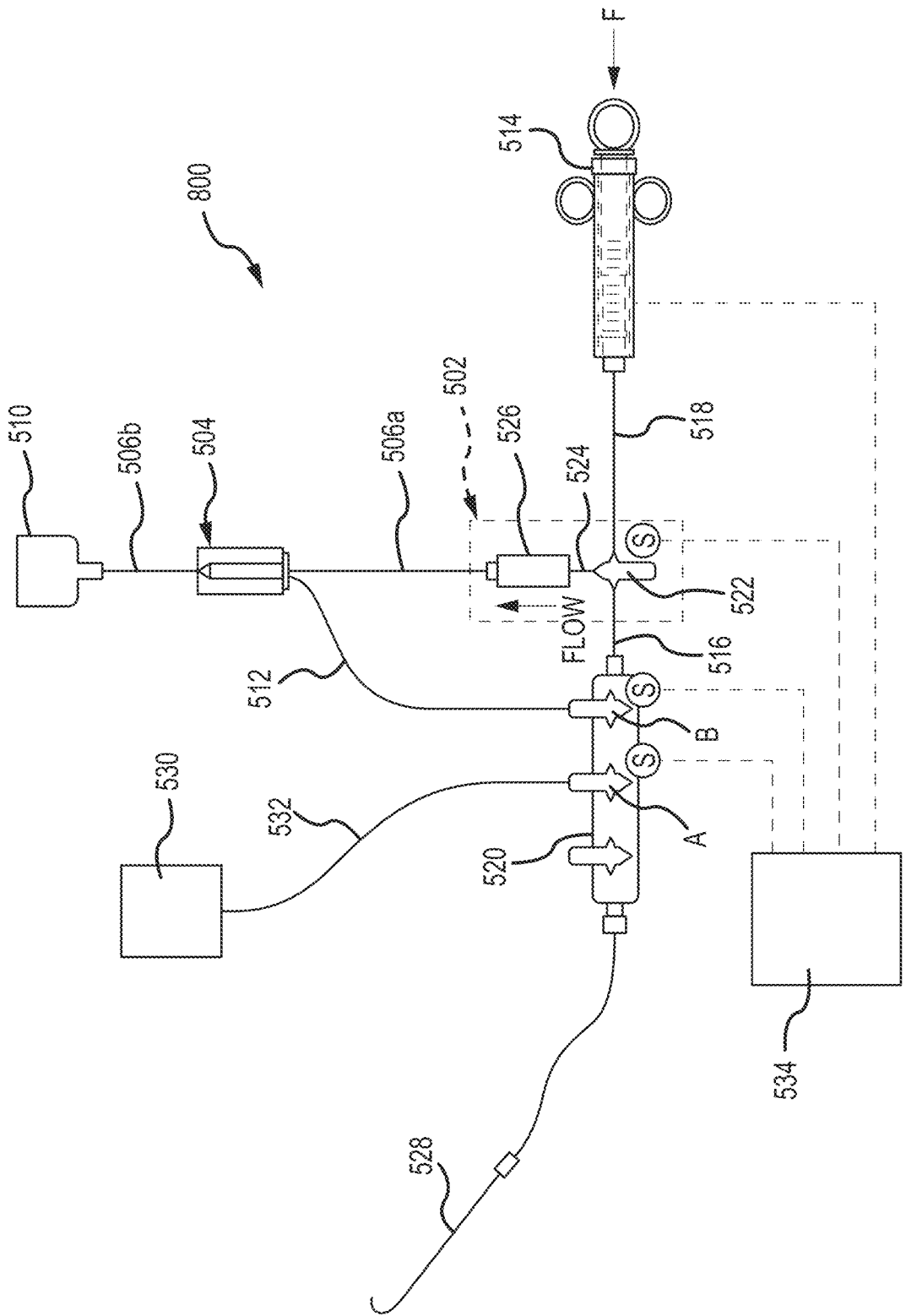
FIG. 8 illustrates an exemplary medium management system.
Figure 9C:
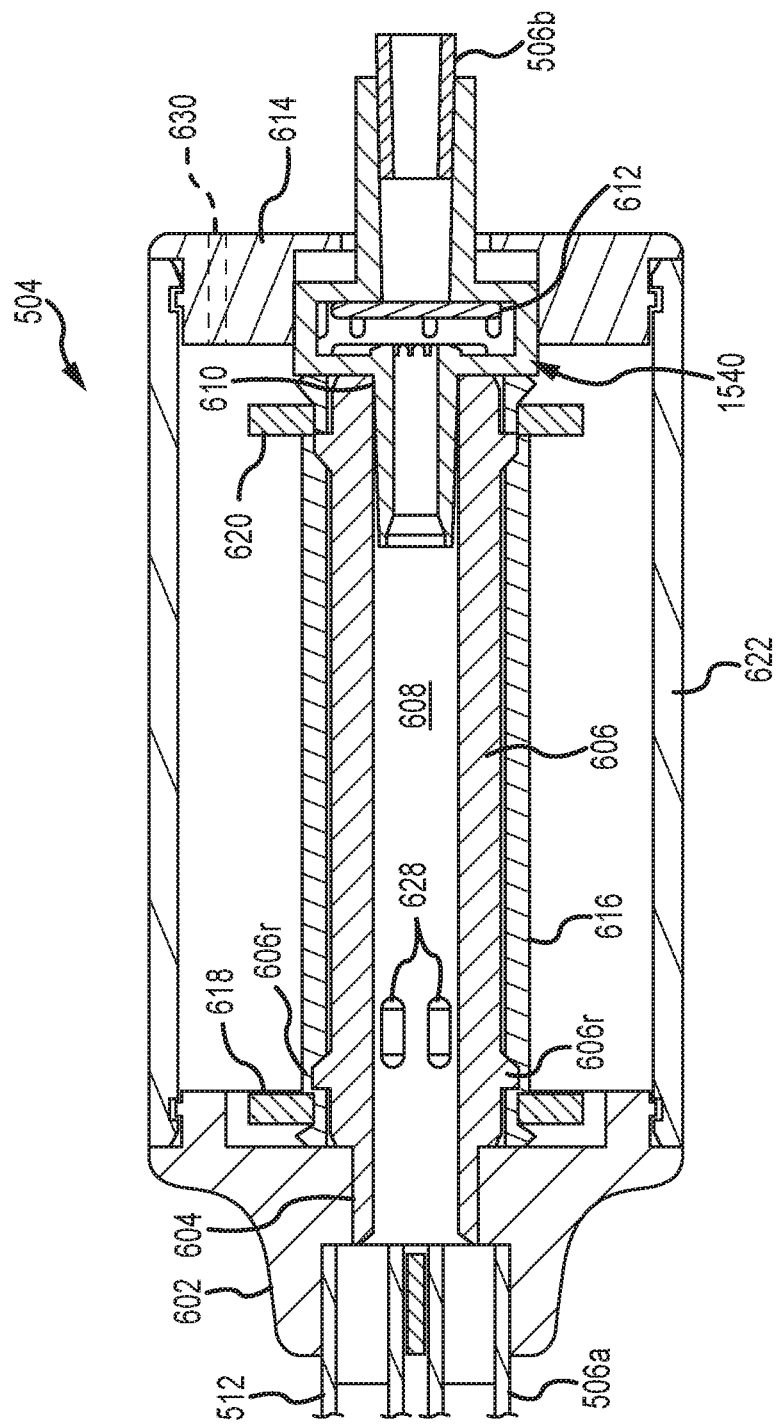
FIG. 9C is a cross-sectional view of the exemplary medium diversion reservoir in a first configuration, taken along line 515C-515C of FIG. 9A.
Figure 9D:
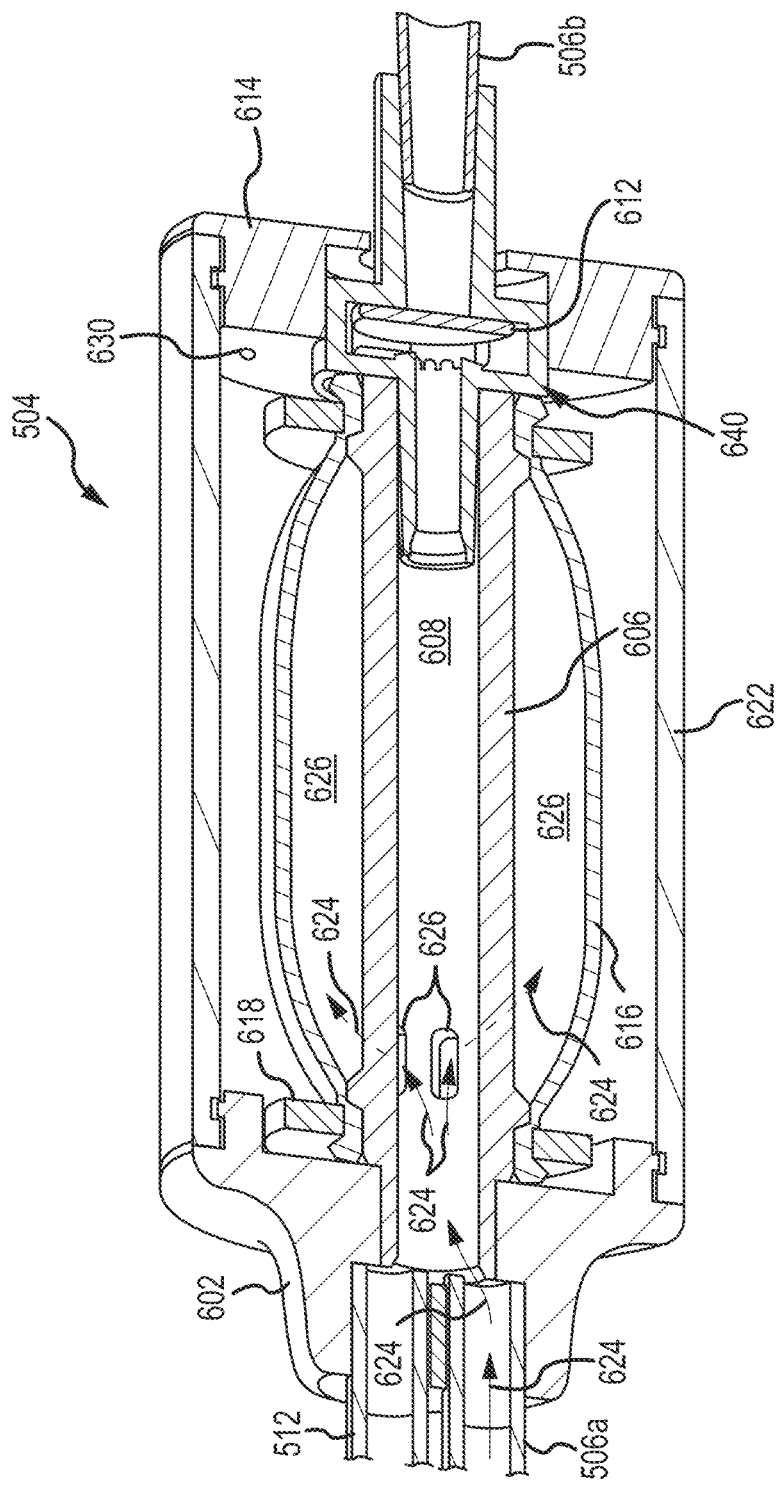
FIG. 9D is a cross-sectional view of the exemplary medium diversion reservoir in a second configuration, taken along line 515C-515C of FIG. 9A.
Figure 10:
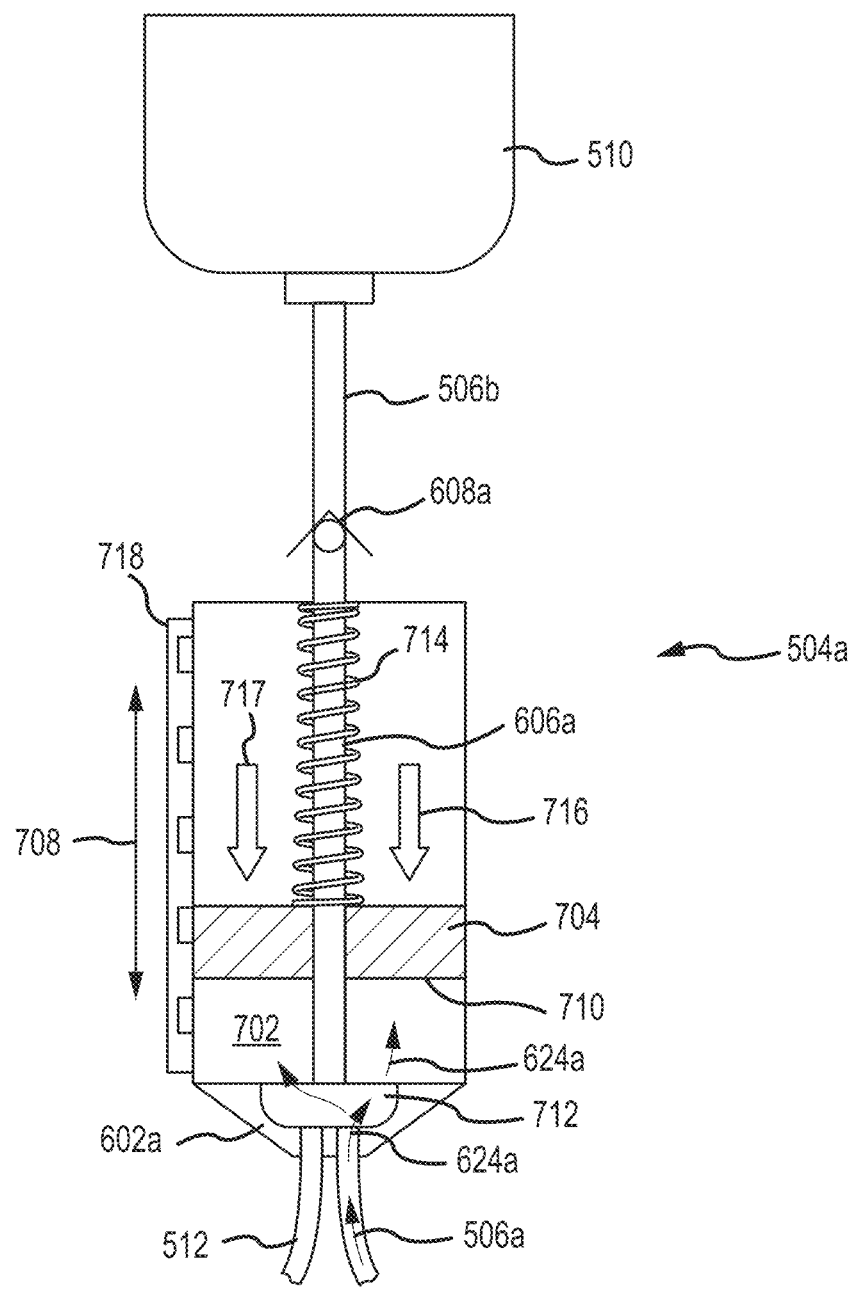
FIG. 10 illustrates another exemplary medium diversion reservoir.

FIGS. 8-10 illustrate another medium management system 500 that may include, as shown in the illustrated embodiment, a flow diverter assembly (i.e., a modulator) 502 and a diversion reservoir 504. In this embodiment, tubular member 506a extends from the valve 526 of the flow diverter assembly 502 to a medium diversion reservoir 504, and tubular member 506b extends from diversion reservoir 504 to medium reservoir (e.g., contrast agent vial) 510.

Medium from the medium reservoir 510 (e.g., contrast agent vial) is permitted to flow away from the medium reservoir 510 and through diversion reservoir 504 via tubular members 506b and tubular member 512. In the illustrated arrangement (of FIG. 8), injector syringe 514 may be fluidly coupled to medium reservoir 510 by tubular members 506b, 512, 516 and 518, coupling those components together by a manifold 520 and through stopcock 522. When the syringe 514 is being loaded with medium from medium reservoir 510, the stopcock 522 may be positioned to permit medium flow between tubular members 516 and 518, but not to tubular member 524 disposed between the stopcock 522 and the valve 526 of the flow diverter assembly 502. The syringe 514 may be any of the monitoring syringes described herein (e.g., using light sensors, Hall sensors, etc.) or of the monitoring syringes known in the art. Drawing back the syringe 514 may pull medium from the medium reservoir 510 through tubular member 506b, and/or diversion reservoir 504, and through tubular member 512.

Medium from the medium reservoir 510 and/or medium residing in the diversion reservoir 504 may then be further drawn, into and toward, syringe 514 through tubular members 516 and 518. Once the syringe 514 is loaded with medium from medium reservoir 510 and/or diversion reservoir 504, valve B on manifold 520 may then be manipulated to prohibit flow back to medium reservoir 510 and diversion reservoir 504 via tubular member 512 (and such flow may be further inhibited by a check valve disposed between diversion reservoir 504 and medium reservoir 510), and the stopcock 522 may be positioned to allow flow through the tubular members 518, 524, 516 and manifold 520.

During contrast injection procedures (where the syringe 514 plunger is acted upon by a force F) incorporating a modulator (such as flow diverter assembly 502) a portion of the injected medium flow from the syringe 514 may be diverted away from the medium flow path to injection catheter 528 by the flow diverter assembly 502. In the modulation/reservoir system 500 illustrated in FIGS. 8-10, such diverted medium flow passing through the flow diverter assembly 502 flows into the diversion reservoir 504, as opposed to the diverted medium flowing directly into the medium reservoir 510 or some other outflow/overflow reservoir/chamber. Advantageously, the diversion reservoir 504 provides means for collecting overflow medium diverted by the flow diverter assembly 502, for possible re-use as the syringe 514 may be again activated to pull medium into the system (e.g., for introduction into the patient via catheter 528). The use of such a diversion reservoir in this manner, with an associated check valve preventing back flow of medium into the medium reservoir 510, allows for capture and re-use of medium that is already introduced into the system (e.g., in the diversion reservoir 504) while preserving the integrity of the medium disposed within medium reservoir 510 in its original form.

The medium management system 500 may also include a saline reservoir 530 that can be used to flush portions thereof. In the depicted system 500 of FIG. 8, the saline reservoir 530 is connected to the manifold 520 via a tube 532 and can be isolated from the remainder of the system 500 with valve A. Although the previously described injection, diversion, reuse of a medium and saline flushing of the system may be performed by mechanically actuating the various valves of the system (i.e., valves A, B, 522 or other valves employed to direct flow) and turning on/off the measurement sensors attached to the diversion reservoir and the injector, the automation of the measurement system with valve sensors may significantly reduce any measurement or non-measurement errors in determining the amount of injection of a medium into a patient. As discussed previously, close monitoring and measurement of contrast injected into a patient can significantly affect the outcome of a patient undergoing a procedure using injected contrast medium. To this end, valve A may include a position or other sensor S that detects a position of the valve A. A flush signal is sent from the valve A sensor S to a monitoring/display system 534, which also may be configured to monitor the position of valve B and stopcock 522 (using sensors S), as well as the output from the various sensors on the monitoring syringe 514 and/or the sensors on the diversion reservoir 504. For example, when the valve A is in an open position, the monitoring/display system 534 may disregard signals from the monitoring syringe 514 and/or diversion reservoir 504 (as those readings are not reflective of contrast being injected from or drawn into the syringe 514). In another example, if the valve A is in an open position, the monitoring/display system 534 may display an instruction or emit a signal to remind an operator to close valve B and/or stopcock 522 so as to isolate those portions of the system 500. In another, more complex example, the system 500 uses automated valve B and/or stopcock 522 and closes these valves upon receiving an open signal from valve A.

One embodiment of the diversion reservoir 504 is illustrated in FIGS. 9A-9D. FIG. 9A shows an assembled view of diversion reservoir 504 along with its associated tubular members 506a and 512. FIG. 9B is an exploded view of the assembly of FIG. 9A The system 500 may further include a second supply conduit 512 in fluid communication with the supply conduit 506b and the diversion conduit 506a, wherein the second supply conduit 512 is fluidly coupled to the fluid medium flow path. Tubular members 506a and 512 are sealably connected to a first end cap or manifold 602 on diversion reservoir 504, as further shown in FIG. 9C, which is a sectional view taken through lines 515C-515C in FIG. 9A A first end of a through-tube 606 is sealably connected to an interior side of first end cap 602, as at 604.

Through-tube 606 includes an inner conduit 608 extending therethrough. Inner conduit 608 is in fluid communication with the interiors of tubular members 506a and 512 via their adjacent couplings in the first end cap 602, as illustrated in FIG. 9C. A second end of through-tube 606 is sealably connected to a check valve assembly 640, as at 610, and the inner conduit 608 is in fluid communication with the check valve assembly 640. The check valve assembly 640 is, in turn, in fluid communication with the tubular member 506a. As seen in FIG. 9C, the check valve assembly 640 includes a moveable valve plate 612 (or other suitable structure allowing one way flow through the valve) which is operable to permit flow from the medium reservoir 510 (e.g., medium contrast vial) via tubular conduit 506b into the inner conduit 608 of through-tube 606, but to inhibit flow in reverse thereof. This arrangement may allow flow of medium from fluid reservoir 510 via tubular conduit 506b, inner conduit 608 of through-tube 606, and tubular conduit 512 to the syringe 514. Moreover, medium flow diverted by flow diverter assembly 502 may also be permitted to flow via tubular member 506a into inner conduit 608 of through-tube 606, but inhibited from flowing to the medium reservoir 510 by check valve assembly 640. A second end cap 614 on diversion reservoir 504 is secured about the check valve assembly 640.

The diversion reservoir 504 is designed to accommodate flow of medium from the flow diverter assembly 502, to collect and hold such medium and then, if desired, urge such collected medium back into the system for use in delivering additional medium to the patient via injection catheter 528. In one embodiment to accomplish this end, diversion reservoir 504 may include an elastic expansion tube 616 disposed about through-tube 606. As seen in FIGS. 9C and 9D, expansion tube 616 extends along a portion of a length of through-tube 606. Expansion tube 616 may be formed of silicone (or like flexible) material sealably secured adjacent each end thereof about the through-tube 606 by first and second retention washers 618 and 620, respectively, or by other suitable sealable and mechanical fastening arrangements. An outer surface of the through-tube 606 may include interference elements such as surface features or an annular interference rim 606r (see FIG. 9C) to further facilitate the sealing of the expansion tube 616 to the through-tube 606 via the retention washer 618 and 620.

A housing tubular outer shell 622 may be connected between the first end cap 602 and second end cap 614, thereby covering the expansion tube 616 and other diversion reservoir components therein. The shell 622 may serve to protect the components of the diversion reservoir 504 therein, limit the extent of inflation or expansion of expansion tube 616, and/or (if the shell 622 is either transparent or translucent) allow observation of the condition (e.g., expanded state) of expansion tube 616 therein.

FIG. 9D illustrates the diversion reservoir 504 in perspective sectional view (again, as taken along lines 515C-515C in FIG. 9A) with the expansion tube 616 shown in an exemplary stretched and expanded state, as opposed to its relaxed state shown in FIG. 9C. The expansion tube 616 of the diversion reservoir 504 receives medium flow from the flow diverter assembly 502, via tubular member 506a. This medium flow, as illustrated by flow arrows 624 in FIG. 9D, flows from tubular member 506a into the inner conduit 608 of through-tube 606 adjacent the first end of through-tube 606. Through-tube 606 can be a portion of the medium supply conduit 506b that resides within reservoir chamber 626. Flow out of the through-tube 606 is inhibited at its second end by the check valve assembly 640. However, the supply conduit through-tube 606 may have one or more apertures 628 therethrough which allows an interior of the expansion tube 616 to be in fluid communication with the inner conduit 608 and reservoir chamber 626. Medium from the flow diverter assembly 502 can thus flow through apertures 628 and into a medium reservoir or chamber 626 defined by the expansion tube 616. This medium chamber 626 is defined between the inner surface of expansion tube 616 and the outer surface of through-tube 606, whereby the expansion tube 616 forms an elastic bladder disposed around the supply conduit 606, with the walls of expansion tube 616 capable of imparting a force on the fluid medium within the chamber 626. A surface within chamber 626 is capable of imparting a variable or constant force on the fluid medium within the chamber 626, and the surface is defined at least in part by a wall of the elastic bladder of expansion tube 616. The medium chamber 626 thus receives and collects the diverted portion of the flow of medium from the flow diverter assembly 502. The diversion reservoir 504 comprises a variable or constant force biasing member disposed relative to at least one surface within the reservoir chamber 626 to urge the surface against the fluid medium within the reservoir chamber 626. The expandable wall of the expansion tube 616 thus defines a surface within the medium chamber 626 capable of imparting a force (variable or constant) on the fluid medium within the medium chamber 626. In one embodiment, the second end cap 614 includes an aperture 630 therethrough to permit the escape of gas within the cover 622 and thereby readily permit expansion of the expansion tube 616 therein.

In use, as the pressure of medium within the flow diverter assembly 502 increases enough to allow flow therethrough, medium flows from the diverter valve 526 via the tubular member 506a to the diversion reservoir 504. Fluid coupling is provided by a medium supply conduit 506b disposed between, and fluidly coupled to, the diversion reservoir 504 and the sterile medium container 510. A diversion supply conduit 506a is disposed between, and fluidly coupled to, the diversion reservoir 504 and the flow diverter assembly 502 so as to supply the reservoir 504 with the diverted portion of the fluid medium from the flow diverter assembly 502. Medium flows within the diversion reservoir 504 as illustrated by arrows 624 into medium chamber 626, thereby stretching the walls of the expansion tube 616 and expanding chamber 626 to accommodate the diverted medium flow. Accordingly, as the medium pressure provided via injector 514 increases in the system, the flow diverter assembly 502 relatively diverts medium so that the flow to the patient relatively increases as relatively less flow is diverted by the flow diverter assembly 502 into the diversion reservoir 504. The medium contained in the chamber 626 may be available for further infusion into the patient via the modulation/reservoir system 500. As an example, an operator may activate valve B to allow medium flow from the chamber 626 of the diversion reservoir 504 into the syringe 514 (which is being withdrawn to draw such fluid therein). If the fluid needed is greater than the volume retained within the chamber 626, the force of check valve 612 is overcome and further medium is withdrawn from the medium reservoir 510 (e.g., contrast agent vial). Once a sufficient amount of medium has been withdrawn from the chamber 626 and/or reservoir chamber 510, valve B may be closed and the modulation/reservoir system 500 may be again in condition for delivery of medium via injection catheter 528, by activation of injection syringe 514 by an operator. As long as the stopcock 522 is disposed to allow flow into tubular members 516 and 524, the flow modulator assembly 502 may automatically activate to divert excess medium, thereby ultimately reducing the amount of medium introduced into the patient via injection catheter 528 (e.g., thus introducing no more medium than necessary to attain operative opacity). In one embodiment shown, as the pressure is increased in the modulator 502, the resistance to medium flow into the diversion circuit is increased by operation of the flow diverter assembly 502. The process may be repeated by an operator as many times as deemed necessary to complete the procedure desired. Use of the modulation/reservoir system 500 in this manner may achieve the advantageous reduction of introduction of unnecessary medium into the patient while achieving the necessary amount and flow of medium in the patient for diagnostic or treatment means (e.g., for opacity). In addition, the diversion reservoir 504 may allow re-use of the diverted outflow of medium.

The diversion reservoir illustrated in FIGS. 9A-9D presents one form of such a reservoir. Alternative forms are contemplated as well. For example, an alternative form of elastic bladder or elastic surface may be provided that functionally allows the receipt of medium overflow from the flow diverter assembly 502 into an expansion chamber, and then further allows the flow of medium from the medium reservoir 510 through the diversion reservoir 504 and into the modulation/reservoir system 500 for use. An alternative means of placing force on the medium within the chamber in the diversion reservoir 504 may be attained by a bias plunger, such as illustrated schematically in FIG. 10 as 504a. The diverted portion of the fluid medium flows through a diversion conduit 506a away from the flow diverter assembly 502. The system 500 comprises a medium reservoir 510 containing a supply source of fluid medium for the system 500 and a supply conduit 506b through the reservoir chamber 702 that fluidly connects the medium reservoir 510 and the diverter conduit 506a. The supply conduit 506b comprises a check valve 608a to prevent the flow of fluid medium from the supply conduit 506b into the medium reservoir 510. Diversion reservoir 504 includes a plunger 704 slidably disposed in housing 706 and moveable in a linear fashion relative to the housing 706, as illustrated by movement line 708. Thus, the surface 710 is movable in a linear direction relative to the fluid medium within the reservoir chamber 702. A proximal face or surface 710 of the plunger 704 thus defines a portion of a chamber 702 within the housing 706 for diverted medium that is received therein via the tubular member 506a.

Like the diversion reservoir 500 illustrated in FIGS. 9A-9D, diversion reservoir configured with a bias plunger 504a may include a first end cap 602a that acts as a manifold for medium flow. Tubular member 506a is connected to first end cap 602a, as is tubular member 512. Chamber 702 is in fluid communication with the interiors of tubular members 506a and 512, such as via manifold 712 within the first end cap 602a, as seen in FIG. 10. A through-tube 606a is also in fluid communication with the manifold 712, and extends through the housing 706 of the diversion reservoir configured with the bias plunger 504a to a check valve 608a. Check valve 608a permits medium flow from medium reservoir 510 via tubular member 506b into through-tube 606a but prevents backflow.

Medium from the medium reservoir 510 can then flow from the diversion reservoir 504a into the syringe 514 via tubular member 512. When medium is diverted by the flow diverter assembly 502 into the diversion reservoir 504a, medium flows as illustrated by flow arrows 624a from tubular member 506a, through manifold 712, and into the chamber 702. The diversion reservoir 504a comprises a variable or constant force biasing member such as spring 714 disposed relative to at least one surface 710 within the reservoir chamber 702 to urge the surface 710 against the fluid medium within the reservoir chamber 702. In an exemplary embodiment, surface 710 is planar. The face 710 of the plunger 704 is biased by spring 714 toward the manifold chamber 712, and thus defines a moveable surface 710 for the chamber 702 that can move away and expand chamber 702 as more medium is introduced therein, when the bias of the force acting against it is overcome. This bias acts on the plunger 704 within the housing 706, as illustrated schematically by force arrows 716, 717 and such force may be achieved by suitable means such as springs, weight distribution, linear actuator, or other force elements. The use of a linearly moving plunger 704 (as its movement is illustrated by arrows 708) may permit more ready measurement of how much medium has actually been diverted by the flow diverter assembly 502 and thereby, by derivation, how much medium has actually been delivered to a patient by the injection catheter 528. Measurement may be performed by utilizing a light-based, Hall sensor-based, or other type of monitoring system 718 disposed in or on the housing 706, or in or on other structures (such as the plunger) of the diversion reservoir 504, as such systems are described herein. The plunger 704 thus provides a linear expansion element (surface 710) that serves to apply force to the overflow medium collected for possible re-use in the chamber 702.

The diversion reservoir 504a operates in a similar manner to the diversion reservoir 504, discussed above, by providing an expandable chamber for medium diverted by the flow diverter/modulating assembly 502, wherein the chamber (e.g., chamber 702, 626) may have at least one surface acting upon it to urge the medium therein back toward the injection device 514 (via conduit 512) for possible re-use. Likewise, medium which has been diverted by the flow diverter assembly 502 into the diversion reservoir chamber 702 is not permitted to flow back to the diverter assembly 502, nor to flow to the medium reservoir 510 (via check valve 608a). In alternative embodiments for modulation/reservoir systems, the diversion reservoir is configured so that flow through it to the medium reservoir 510 is not permitted or necessary.

Figure 11:
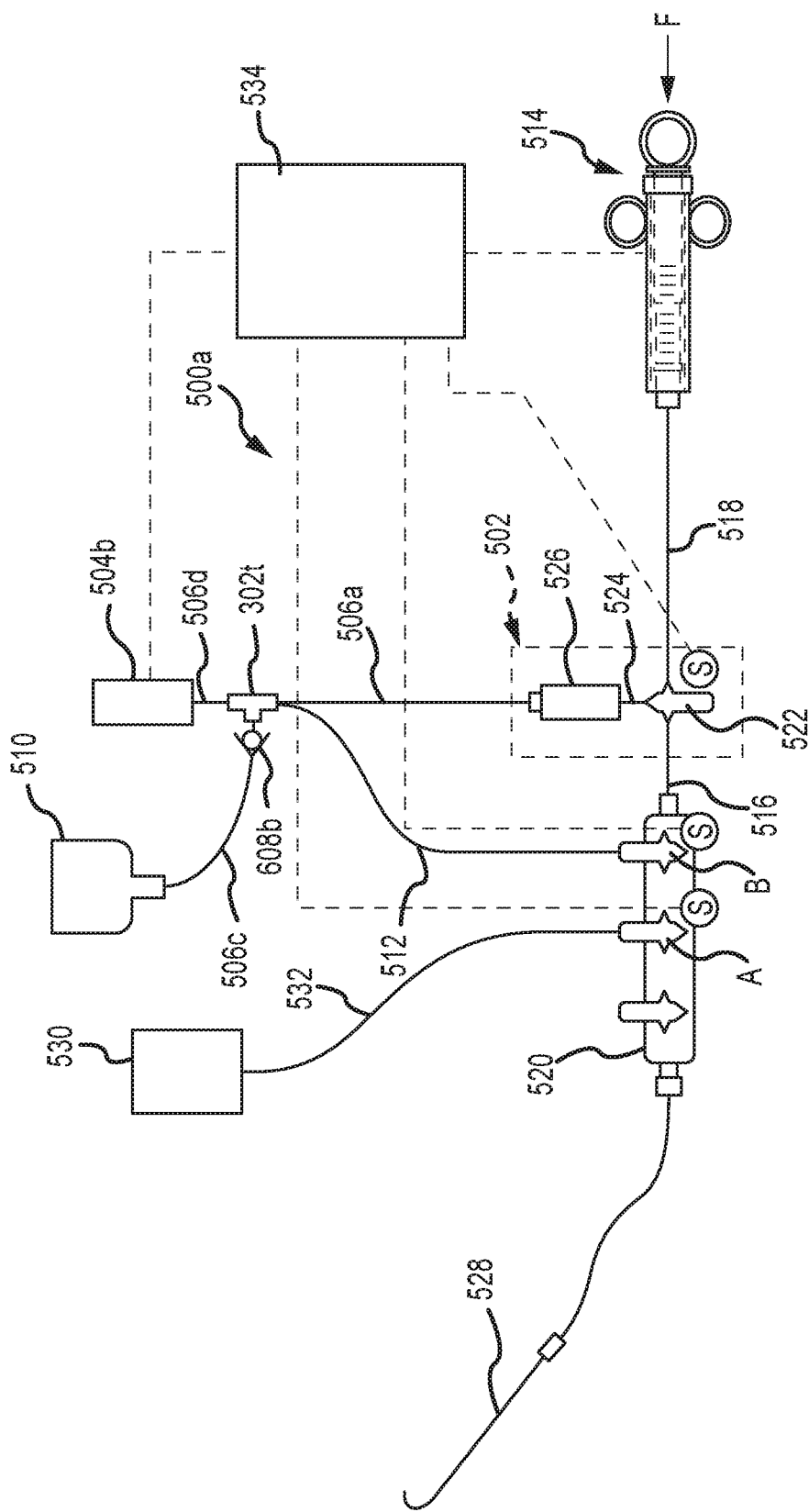
FIG. 11 illustrates another exemplary medium management system.

One such arrangement is illustrated in FIG. 11, in connection with a modulation/reservoir system 500a. In these arrangements, there may be no necessity for a through-tube arrangement through the diversion reservoir. The diversion reservoir may simply provide an expandable chamber therein for retaining and re-using medium diverted from the flow diverter assembly 502. Such diversion reservoirs 504b may employ a bladder form of chamber or a constant or variable force resistance form of chamber, such as those illustrated and discussed herein, where at least one surface therein is capable of imparting a sufficient force upon the fluid medium within the chamber. For example, the diversion reservoir 504b may be constructed to function similar to the spring-based monitoring syringe 300 depicted in FIG. 5. Although the "injection function" of the syringe 300 may not be needed to function as a diversion reservoir, one can see the advantages of using the measurement capabilities derived from the chamber as described in FIG. 5 as it might function as a "diversion reservoir", utilizing spring 309 to bias piston 310. FIG. 11 illustrates an arrangement where the medium reservoir chamber 510 is connected via tubular member 506c to a T-connector 302t disposed between a diversion reservoir 504b (without a through-tube) and the flow diverter assembly 502. The T-connector 302t connects at its first end to the tubular members 512 and 506a and at its second end to tubular member 506d that leads to the diversion reservoir 504b. A side fitting of the T-connector 302t leads via tubular member 506c to the medium reservoir 510. A check valve 608b is disposed between the T-connector 302t and the medium chamber 510 to prevent back flow of medium from the flow diverter assembly 502 and/or diversion reservoir 504b into the medium container 510. In operation, the configuration illustrated in FIG. 11 may be similar to that described above with respect to FIG. 8, in that a force F ejects medium from the syringe 514. As the pressure of medium within the flow diverter assembly 502 increases enough to allow flow therethrough, medium flows from the valve 526 via tubular member 506a to the T-connector 302t. Medium may then flow from the T-connector 302t via tubular member 506d to the diversion reservoir 504b. Medium flowing into the diversion reservoir 504b moves the piston therein to accommodate the diverted medium flow. In operation, medium provided via syringe 514 may be diverted by the flow diverter assembly 502 away from injection to the patient, and accumulate in the diversion reservoir 504b.

The medium contained in the expandable chamber within the diversion reservoir 504b may be available for further infusion into the patient via the modulation/reservoir system 500a. To do so, an operator activates valve B to allow medium flow from the chamber within the diversion reservoir 504b into the injector syringe 514 (which is being withdrawn to draw such fluid therein). If the fluid needed is greater than the volume retained in the chamber reservoir 504b, the force of check valve 608b is overcome and further medium is then withdrawn from the medium reservoir 510. Once a sufficient amount of medium has been withdrawn from the chamber within the diversion reservoir 504b and/or reservoir chamber 510, valve B is again closed and the modulation system 500a is again in condition for delivery of medium via injection catheter 528, by activation of injection syringe 514 by an operator. As long as the stopcock 522 is disposed to allow flow into tubular members 516 and 524, the flow diverter assembly 502 will then again be automatically activated to divert excess medium when a threshold pressure for activation of the flow diverter assembly 502 is attained, thereby ultimately reducing the amount of medium introduced into the patient via injection catheter 528. Again, as pressure is increasing going into flow diverter system 502, the flow through the diverter 502 is relatively decreasing (thus, flow to the patient may be relatively increasing at the same time by operation of the flow diverter assembly 502). The process can be repeated by an operator as many times as deemed necessary to complete the procedure desired. Use of the modulation/reservoir system 500a in this manner achieves the advantageous reduction of introduction of unnecessary medium into the patient while achieving the necessary amount and flow of medium in the patient for the desired diagnostic or treatment process. Furthermore, the modulating/reservoir assembly may advantageously allow an operator to change out the injection delivery system (i.e., guide catheter, diagnostic catheter, treatment tools, etc.) without changing the flow modulator.

Figure 12:
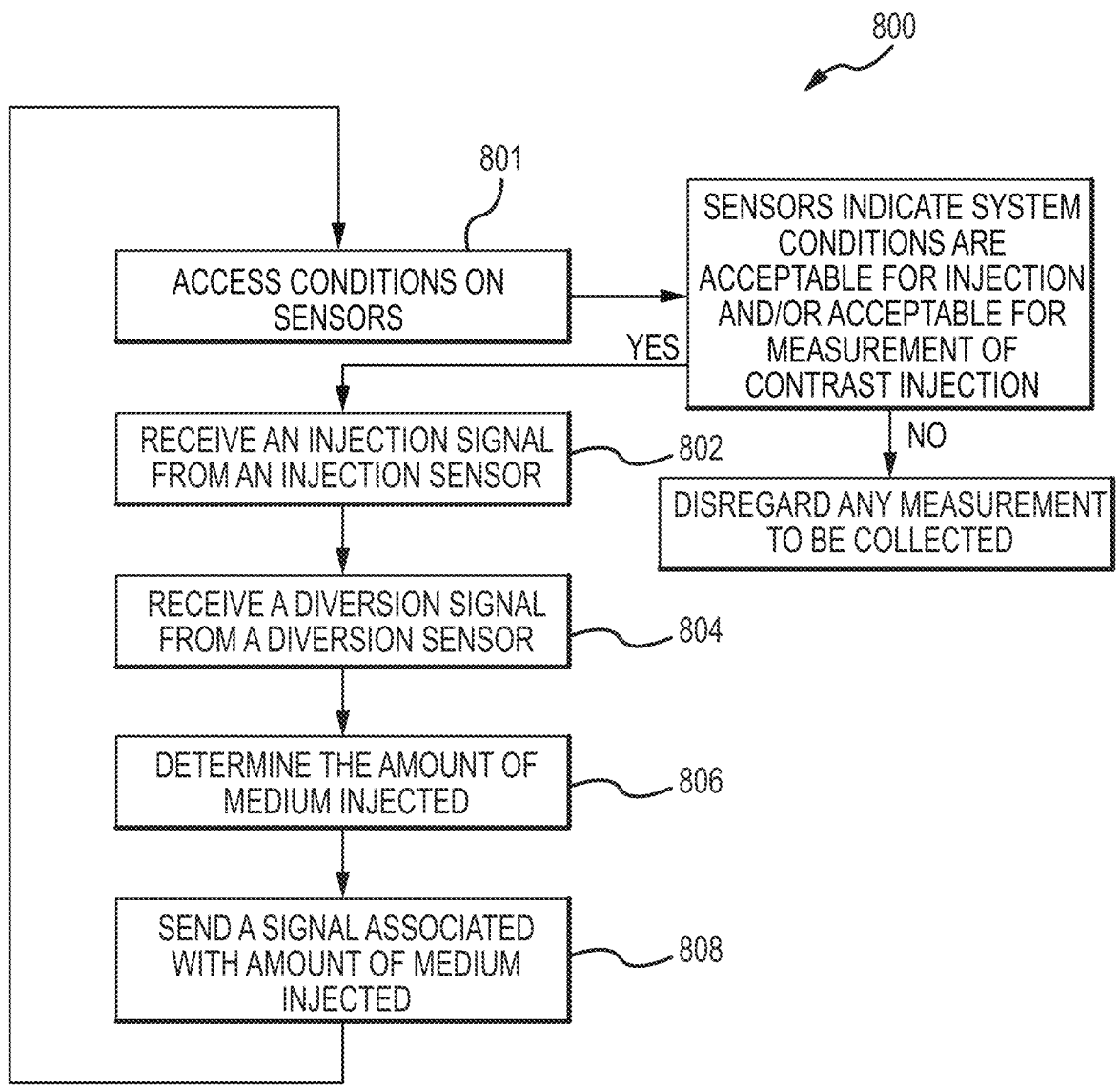
FIG. 12 depicts a method of determining an amount of medium injected into a patient.

Moreover, the diversion reservoir may allow simplistic re-use of the diverted medium. FIG. 12 depicts a method 800 of determining an amount of medium injected into a patient. The method begins at operation 801, where an assessment is made on conditions of the valve and/or toggle sensors of the system. If the toggle or valve sensors indicate that the system is set for an injection of medium (e.g., the diversion apparatus is set to function and the saline apparatus is closed or not allowing passage of saline) measurement of the media will continue with operation 802, where an injection signal(s) is received from a sensor associated with an injection syringe. If the toggle/valve sensors of 801 indicate these conditions are not met, the measurement system will assume flushing of the system and it will disregard any measurement data. If the sensors suggest the system is ready for an injection, operation 804 will follow (or proceed simultaneously) operation 802 wherein a diversion measurement signal(s) is received from a sensor associated with a diversion reservoir. Each of the injection signals and the diversion signals may be received from the various types of monitoring systems as described herein, including light-based sensor systems, Hall sensor-based systems, and so on. These signals can include position signals (e.g., position of the piston), which may be used to determine a volume of medium contained within the injection syringe and/or the diversion reservoir. With this information, the amount of medium injected may be determined based at least in part on the injection signal and the diversion signal, in operation 806. In an example, the amount injected is the difference between the change in volume in the injection syringe minus the change in volume in the diversion reservoir. Operations 801-806 are constantly updated as medium is injected into the patient.

In operation 808, a signal associated with the amount of medium injected is sent. The summation of the total amount medium injected in a patient over time can be maintained. Signals and measurement data may be provided to an operator in the form of an audible or visual signal which can indicate to the operator of the system (i.e., a surgeon or technician) the amount of fluid injected. The signals can include a visual display of the amount injected (e.g., on a monitoring display), or a signal that may indicate to the user that a maximum amount of contrast has been injected, or that none of the medium ejected from the syringe has been received in the diversion reservoir (which may be an indication of a valve or system problem). The systems described herein also include a saline flush system. Saline volumes passing through the system should be ignored so the amount of medium injected is not incorrectly calculated. As such, the method 800 contemplates receiving a flush signal or 801 wherein the valve or toggle sensors indicate conditions exist to allow flushing; or conversely, conditions exist to allow an injection of medium. Depending on the assessment of sensor conditions, subsequent injection signals and/or diversion signals are disregarded based at least in part on the received flush signal, or similar indicator(s). The injection and/or diversion signals may be ignored while the flush signal is still received, which allows the operator to flush the system without the saline volume passing through the system causing a miscalculation of the injected medium. In an optional operation, a position of at least one valve based at least in part on the flush signal may be adjusted, if automated valves are being utilized in the system.

Otherwise, in systems where manual valves are used, the flush signal received in operation 801 may cause a signal to be emitted, which may be used to signal an operator to close the valves not associated with the flush system (e.g., valve Band stopcock 522 in FIG. 8). Further, it is assumed that it is understood that the order of the steps in FIG. 12 maybe performed in a different order as shown without deterring from the scope of the invention. As an example, without being wholly inclusive, one might collect data from the diversion sensor before the injection sensor.

The monitoring systems described herein may be utilized to deliver any types of fluids to a patient during a medical procedure. Such fluids may include medium (media), agents, substances, materials, medicaments, and the like. It should be noted that these terms are used generically herein to describe a variety of fluidal materials that may include, at least in part, a substance used in the performance of a diagnostic, therapeutic or/and prophylactic medical procedure and such use is not intended to be limiting. It should be understood that the medium delivery modulation and/or measurement devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain.

The materials utilized in the manufacture of the monitoring syringe may be those typical in medical applications. Plastics such as polycarbonate may be utilized for the syringe housing and plunger. The band or gradation may be printed directly on the plunger shaft, or may be printed on a discrete plastic sheet or sheath that may then be affixed to the plunger shaft. Various types of printing may be utilized to change the translucency or opacity of the band or gradation. In some embodiments, the type of printing may be based on the type of light to be received by the sensors. For example, carbon-based printing may be utilized for sensors that detect infrared light. Thus, the band or gradation may be utilized as the filter described above.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

As discussed previously, various sensors indicating the positioning (or functioning—opening or closure) of the various valves (and/or stopcocks) in the system may help accommodate the measurement of a medium injected by the syringe 514 in a system, with or without a diversion/modulation system. As well as, a system without a diversion reservoir wherein the diversion reservoir may be simply a collection container, or a commercial reservoir, may be attached to the diversion assembly 502. Such a system might look like drawing FIG. 11 wherein the diversion from the diversion assembly 502 through tube 506a may simply end with the T-connector/stopcock 302, or other valving mechanism to facilitate the user in applying their own reservoir. A diversion assembly 1402 as seen in FIG. 15 may be used having the assembly fluid connection lines 1406a and 1412, with a simple connector (i.e., stop cock for example) for attachment to available contrast capture reservoirs that may be available and/or employed by users. FIG. 16 depicts some commercially available reservoirs for capturing contrast, as well as a connection line 1406c that may be used to connect these reservoirs to the diversion assembly. Note that this configuration might not have measurement capabilities, although it would have the benefit of the diversion assembly.

As discussed in FIGS. 8 and 11, a flush signal may be sent from the valve A sensor S to a monitoring/display system 534, which also may be configured to monitor the position of valve B and stopcock 522 (using sensors S), as well as the output from the various sensors on the monitoring syringe 514 and/or the sensors on the diversion reservoir 504a. FIG. 13 illustrates graphically a system utilizing various sensors for the measuring of medium in a system utilizing a diversion reservoir. As seen in FIG. 13, an injection syringe 514 may be used which comprises one or more hall sensors positioned along the axis of the syringe. As described previously, the Hall sensors may be mounted on the housing of the syringe, or on the plunger of the syringe. In the case of FIG. 13, the Hall sensors are mounted on the plunger with a magnet positioned on the housing of the syringe, such as described by 514. The syringe may also be equipped with a Blue Tooth module to coordinate the transfer of information from the syringe Hall sensors to the display unit (also equipped with Blue Tooth communication abilities).

A stopcock or valve 522 fluidly coupled to the syringe 514, manifold 4120 and diversion element 526 may have a sensor S associated with the positioning and/or functioning of the fluid flow from/to the injector 514, diversion valve 526 and the manifold 520. The sensor S may be a rotational sensor that can detect the rotation/position of valve 522. Sensor S of 522 may have electrical connections to the diversion reservoir module 504a, allowing communication to the display/monitoring 200 system through a Blue Tooth connection.

When injecting medium to the patient through catheter 528, valve 522 may allow contrast to flow from the injector through the diversion element/valve 526, as well as through the manifold 520 to the catheter 528. Measurements may be made as to how much of the volume was ejected to the manifold/patient and the diversion valve 526 (and through the diversion line 506a). If stopcock 522 were closed to the diversion valve 526, 522 sensor S would indicate that a measurement of an injection from the syringe 514 should not be measured, for example. In this case, the physician may want to remove saline from a saline reservoir (not shown) to flush the system, while not wanting to tract the saline as a contrast injection. The saline reservoir and connection line (not shown) would typically be connected to Valve A (522A).

During an injection of contrast, medium flow through the diversion line 506a may enter the reservoir chamber 702. The diversion reservoir module 504a may be capable of measuring the volume change within the reservoir chamber 702 through Hall sensors 718. In the illustrated case, the Hall sensors are mounted on the housing of the reservoir chamber and the magnet(s) are mounted on the plunger of the reservoir. However, as discussed previously, the Hall sensors could be a part of the plunger/piston of the reservoir while the magnet(s) are attached to, associated with, or in proximity of the injector housing. The diversion module is equipped with Blue Tooth so as to transfer information to the monitoring/display unit for analysis and/or display.

By measuring the change in the amount of volume from the syringe 514, and the change of volume collected in the reservoir chamber 702, control unit/display can calculate the amount of contrast injected to the patient (via catheter 528). As shown in FIG. 13, diversion line 506 may also incorporate a one-way check valve (if not included as part of the diversion valve 526) so as to allow medium to flow only to the diversion reservoir 504*a*.

Upon the completion of an injection, Valve B 522B may be opened to draw contrast from the diversion reservoir, and if necessary (and secondarily) the dye medium reservoir. In the case shown in FIG. 13, a pressure transducer acts as the position sensor for stopcock valve B 522B. When contrast line 512 is opened, to draw medium into syringe 514, pressure sensor of Valve B 522B senses a change in pressure and indicates that both the diversion reservoir and injection syringe Hall sensing elements should be activated. The information from the sensor of Valve B may be attached by an electrical coupling to a Blue Tooth element in the Diversion Reservoir Module 504*a* so as to transfer information via Blue Tooth to the display system on its status. As described previously, the medium drawn from the diversion reservoir chamber 702 may proceed any medium drawn from the contrast medium reservoir 504, so long as there is medium in the diversion reservoir chamber 702. Note also, a one-way valve may be attached along contrast supply line 506*a* to allow the medium to only flow in the direction of the diversion reservoir (e.g., if the valving mechanism is not part of the diversion reservoir 504*a*).

FIG. 13 also shows a "Pause Button" associated with the diversion reservoir. The pause button allows a user to override any injection/measurement so as to pause the collection of data by one, or all of the sensors, associated with the Blue Tooth of the diversion reservoir module 504*a*.

The description of FIG. 13 illustrates but one variation of a system using measurements with a system diverting medium to reduce the amount of contrast induced to a patient. It is clear that there may be alternative ways of providing such a system without deviating from the intent of the invention. For example, one might use different sensing systems for the injection syringe or the diversion reservoir. Or, the Hall sensing configurations may be different than described.

Moreover, various sensing elements have been described for identifying the positional relationships of the various valves/stopcocks, including rotational and pressure. It is not intended that these be restrictive in sensing modalities, nor in the placement of the different sensing modalities on the different valves.

The examples herein describe various elements for measuring an injection of a contrast agent; as well as, modulating/diverting medium so as to reduce the total amount of contrast injected into a patient. The descriptions also include various combinations of using of both of these elements together. It should be known to those skilled in the art that various systems may include various elements of diversion and/or measurement. And each of these combinations may or may not include a console, or similar display. Examples (although not to be interpreted as wholly inclusive) of various elements of the described systems might include: the diversion valve alone; the diversion valve with a reservoir; the diversion valve with reservoir and measurement system/sensors; and, measurement without modulation/diversion of medium, to name a few.

Figure 14:
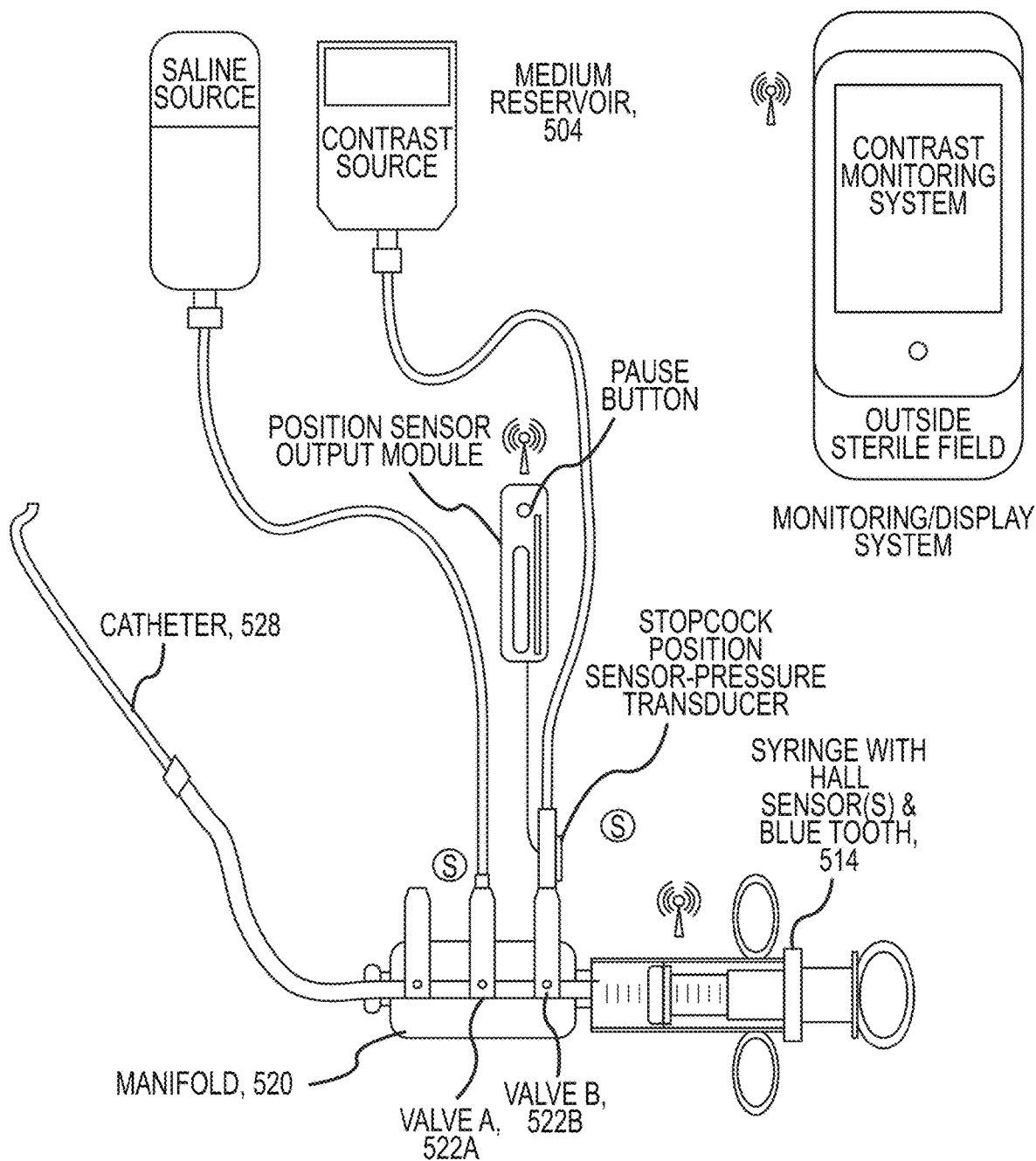
FIG. 14 graphically illustrates an alternative measurement management system.

For example, FIG. 14 describes a system for measuring a contrast medium being injected into a patient. As shown, there is no attempt to modulate or divert the contrast medium being injected into the patient. The measurement system includes a syringe which may be similar to the one shown as 514, having Hall sensor capabilities. It also may have a Blue Tooth elements to connect with the monitoring/display system. In the drawing as shown, a simple pressure transducer (Stopcock Position Sensor) indicates when stopcock valve 522 B position is open/closed. If open (with only a fluid connection to the contrast reservoir), the pressure sensor indicates contrast is being drawn from the contrast medium reservoir 504. If the valve 522B is closed, so as to shut off communication with the contrast medium reservoir 504, the sensor indicates that no more contrast is being drawn into the system (e.g. by the syringe 514). And, further, this data may be sent via Blue Tooth to the display console from the Position Sensor Output module.

Figure 17A:
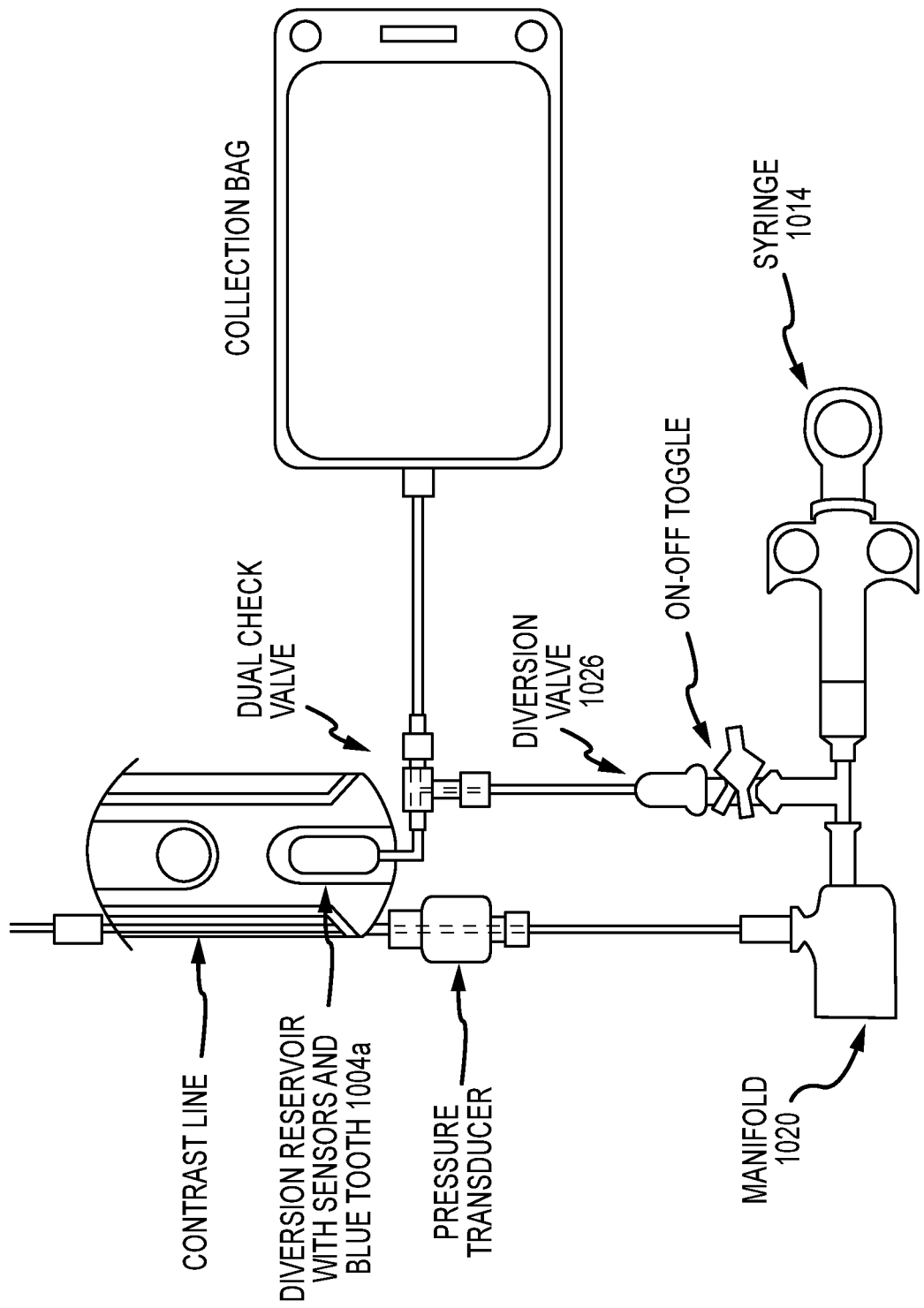
FIGS. 17A and 17B depict another example of a medium measurement system.
Figure 17B:
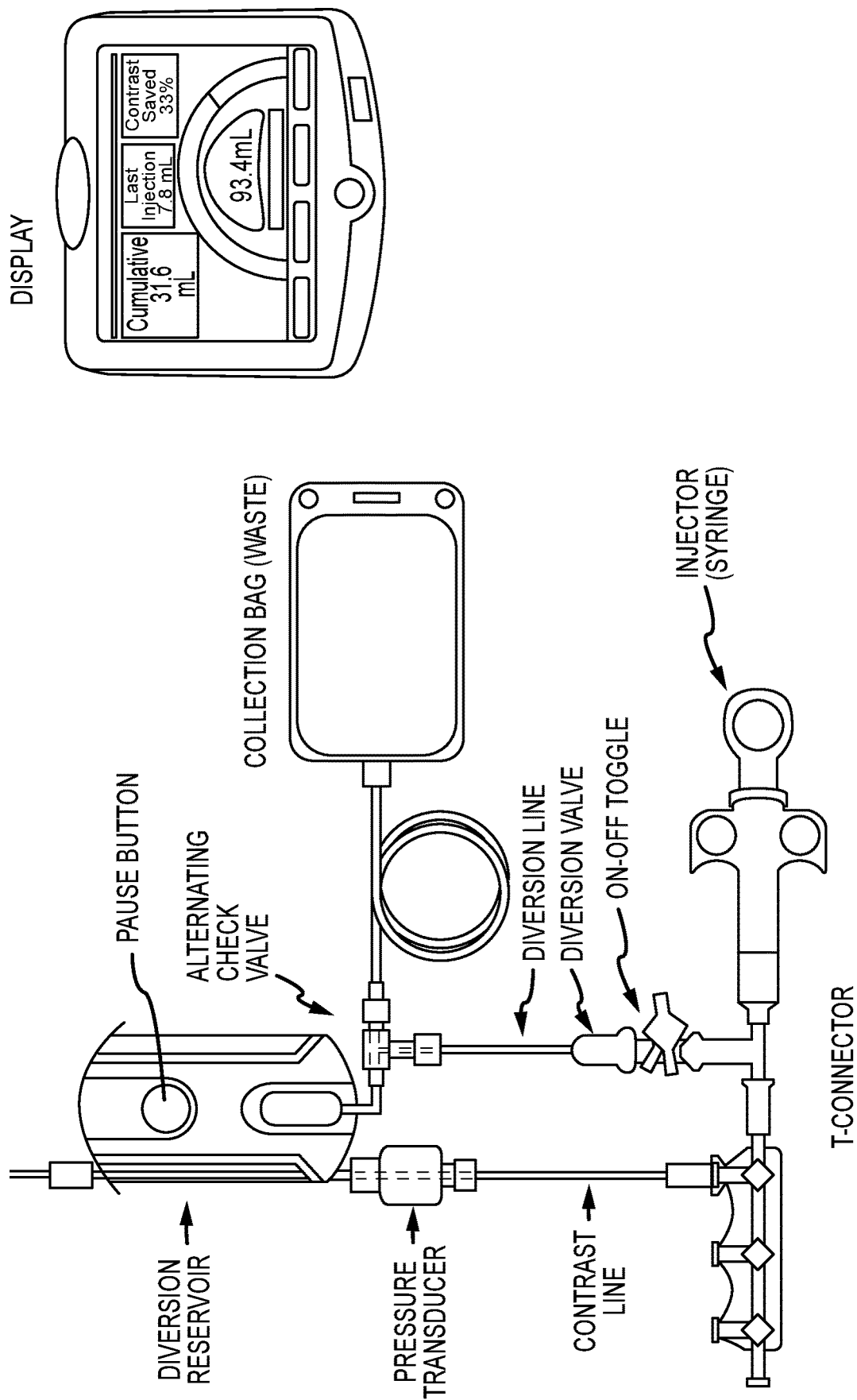

As discussed previously, various components of measurement and/or modulation (diversion) and/or medium capture for reuse have been described and each component may be used to "mix and match" to address various needs of the end user. As an additional example of a preferred embodiment, FIG. 17A depicts a graphical representation of FIG. 17B wherein an end user would prefer to modulate/divert a medium injection into a patient, as well as take measurements of the injected medium. However, the end user may find the effort of priming and purging the fully automated system of FIG. 13 may be more difficult to purge the injection system of air to be a little cumbersome. However, if an end user were only to measure the diverted medium, and not the reservoir medium for reuse (e.g., capture), the priming and purging of the system might be significantly easier by eliminating the flushing of the reservoir and the return conduit back to the injection system for reuse. FIGS. 17A and 17B depict such as system wherein medium may be measured by the syringe and by the diversion reservoir in order to make/determine a measurement of the injection into a patient, as well as disregard measurements when an end user is flushing the system with saline. However, the diverted medium in the medium reservoir is not reused (adding an additional elements in the system, such as the reservoir reuse conduit, that requires priming/purging), and it is subsequently expelled from the injection system into a collection bag as waste. Given that some injection contrasts may be relatively inexpensive, as compared to cath lab time and personnel, some users might prefer to throw away the diverted medium rather than capture the medium for reuse.

As depicted in FIG. 17A and FIG. 17B, contrast line directly from the sterile medium container (or as discussed previously in FIGS. 15 and 16, a line from a sterile reservoir) to the manifold 1020. The contrast line may have a position sensor, such as a pressure transducer to indicate when contrast is drawn from the contrast line. Conversely, with automation of measurements preferred, a position sensor (not shown) could be applied at the connection of the manifold with the contrast line to include a toggle (for on/off of the contrast conduit) with a positional sensor associated with the condition of the toggle. As shown in FIGS. 17A and 17B, syringe 1014 may draw fluid into its chamber for injection. Upon injection to patient from syringe 1014, with the ON-OFF toggle valve open to the diversion valve 1026, medium will be injected to the patient through the delivery conduit (not shown), as well as a portion of the injection will be diverted through diversion valve 1026 so as to modulate/alter the injection medium actually delivered to the patient (e.g., through the delivery catheter). If measurement automation is preferred, the injector and the reservoir may include measurement elements so as to determine the amount of medium ejected out of the injector and received in the reservoir, to determine the amount of medium delivered to the patient. As shown, a dual or alternating check valve may positioned between the reservoir, diversion line, and the collection (waste) bag. In operation, the dual/alternating check valve allow fluid to be diverted to the diversion reservoir 1004*a*, and subsequently (with pressure within the reservoir chamber) re-directed to the collection bag as the injection (from injector) ceases or if the ON-OFF Toggle switch is closed.

Figure 18A:
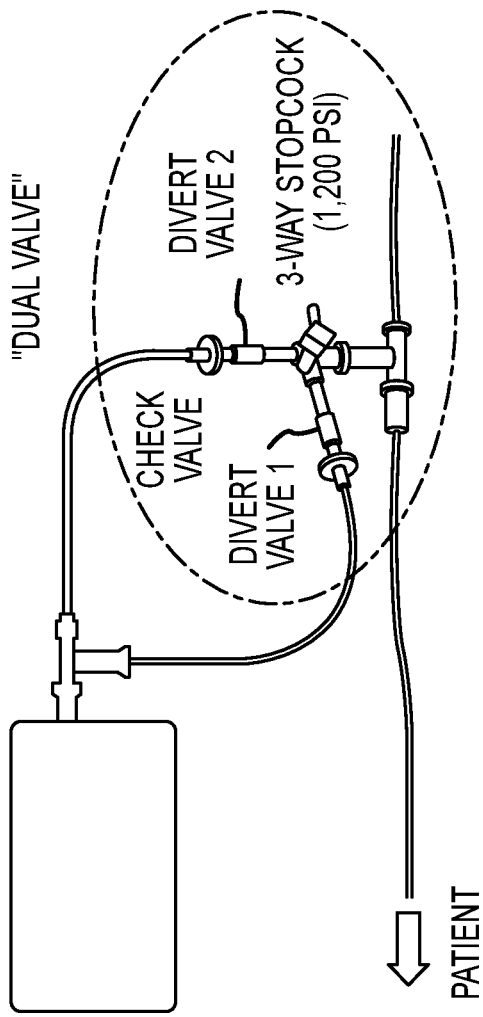
FIGS. 18A and 18B depict another example of a medium measurement system.
Figure 18B:
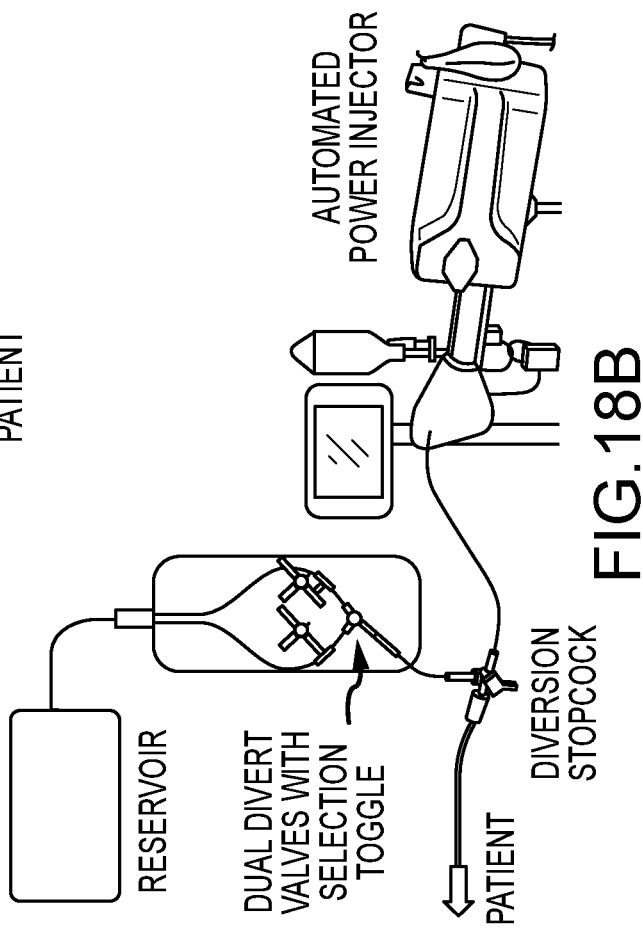

An alternative embodiment can be seen in FIGS. 18A and 18B wherein a diversion of an injection is diverted (a toggle or stopcock may be used to open the diversion flow path) to divert from the injector (not shown in FIG. 18A) to, and through, alternative Diversion Valves of #1 or #2. As depicted in FIG. 18B, a diversion stopcock may allow diversion to a Dual Divert Valve apparatus with the Dual Divert Valve apparatus comprising a valve to direct the flow to two alternative diversion valves. Although, two valves (and therefore two diversion profiles) are depicted, it is clear that multiple divert valves (e.g., 3, 4 or more) may be advantageous to address a great number of user preferences. The valves being discussed are depicted and described as being configured in a parallel fashion. However, one skilled in the art would realize that some valves may be aligned in a serial fashion to obtain the same net result. The diversion valves previously described may accommodate a variety of injections from an injector through a variety of delivery conduits while regulating the diversion of a portion of the injected fluid so as to maintain a relatively constant flow injection to the patient. In such cases, as described previously, the diverter valve is regulating the various flows/pressures of the fluid injected, and the divert valve is regulating the flow to the patient by relatively increasing resistance to diversion with increasing pressure at the divert valve. However, such a configuration may not sufficiently address situations wherein there are large differences in the pressure/flow from the injector, or there are large differences in the operational use to deliver a fluid at largely different rates, or through injection systems wherein the delivery conduit to the patient are vastly different in structure and/or configurations.

Examples of the different uses of the of a diversion systems such shown in FIGS. 18A and 18D might include: the delivery conduit having vastly different dimensional differences such as the delivery of a fluid through an 8F delivery catheter versus a 4F delivery catheter; delivering a medium to one site and then delivering to a second site wherein the intended injection (e.g., flow and or pressure) into the patient are vastly different at each site, such as injections in to the heart versus injections into peripheral vascular sites, or injection to one large coronary branch (RCA) versus another large coronary branch (Left Main, Left Coronary Artery and/or left Circumflex Artery); and, wherein an injector maintains a constant flow and/or pressure (less variable than a syringe), but may require adjusting the injection flow/pressure to assess different vascular sites, such as may encountered with the use of an automated power injector (shown in FIG. 18B).

FIG. 18A depicts a flow diversion having two separate Divert Valves and check valves (to maintain directional fluid flow). In this example, the excess diverted fluid is wasted (not captured for reuse) to a collection bag/reservoir. FIG. 18B further depicts a Diversion Stopcock to access the diversion valves, and further depicts the two Divert Valves mounted onto a single apparatus with a separate toggle to access the different diversion profiles created by the two different Divert Valves.

Although it is not shown in FIGS. 18A and 18B, any of the various positional sensors described previously (whether toggle, flow sensors, pressure transducers, or any other sensors that may determine the conditions of the various conduits and fluid lines) may be utilized in automating measurements of the injection system. During use of the Power Injector as depicted in FIG. 18B, it may be typical to have an end-user change the injection setting for injection into different vascular sites. As an example, the end used might select a constant flow/pressure for injection into the Right Coronary Artery (RCA), and select a different flow/pressure for the Left Coronary Artery (LCA). If the flow/pressure rates differ significantly between the two sites, the end-user may toggle between Divert Valves #1 and #2 to set a different diversion profile to address each site.

It is also understood that any measurement apparatuses, such as those described herein for the diversion reservoir measuring system and the injector measuring system, may also be employed in automating the measurements of fluid delivered to the patient. In addition, if the power injector has a system to measure fluid ejected from the injector, it may be advantageous to coordinate data collection from the injector and a reservoir measurement apparatus (described previously) on a diversion reservoir to automate the measurement of the medium injected to the patient.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

The invention claimed is:
1. A system for measurement automation of a fluid injected into a patient with a fluid injection apparatus, the system comprising:
   a reservoir;
   the fluid injection apparatus comprising:
      a delivery conduit for insertion into the patient and delivery of the fluid into the patient;
      an injector for injecting the fluid into the patient via an injection fluid path fluidly coupling the injector to the delivery conduit;
      a diverter assembly disposed between the delivery conduit and the injector, said diverter assembly configured to divert at least a portion of the fluid away from an injection fluid path between the injector and the delivery conduit, the diverter assembly being fluidly coupled to the reservoir, wherein the diverter assembly is configured to allow at least the portion of the fluid injected by the injector to be simultaneously delivered to the delivery conduit and diverted away from the delivery conduit based on at least one of a pressure and a flow of the injection fluid path, wherein the diverted fluid is stored in the reservoir; and
      a connector fluidly coupling the injector to the diverter assembly and the delivery conduit; and
   a measurement automation apparatus comprising:
      an injector sensor module configured to be applied to a plunger and a housing of the injector, the injector sensor module is configured to generate data for the determination of a volume displacement within the injector;
      a reservoir sensor module configured to be applied to a plunger and a housing of the reservoir, the reservoir sensor module configured to generate data for the determination of a volume displacement within the reservoir;

a processor configured to receive the data generated by the injector sensor module and the data generated by the reservoir sensor module to determine the amount of the fluid delivered to the patient based at least in part on the data generated by the injector sensor module and the data generated by the reservoir sensor module; and a display operatively coupled to the processor for displaying the amount of the fluid delivered to the patient.

2. The system of claim 1, wherein the injector sensor module comprises a hall sensor disposed on the plunger of the injector and a magnet disposed on the housing of the injector.

3. The system of claim 1, wherein the reservoir sensor module comprises a hall sensor disposed on the plunger of the reservoir and a magnet disposed on the housing of the reservoir.

4. The system of claim 3, wherein the plunger of the reservoir is biased towards a fluid inlet of the reservoir.

5. The system of claim 1, wherein at least one of the injector sensor module and the reservoir sensor module comprise a light sensor module.

6. The system of claim 1, further comprising a manifold coupled to the injection fluid path, wherein the manifold comprises at least one actuatable valve.

7. The system of claim 6, further comprising a contrast return line fluidly coupling the reservoir and the at least one actuatable valve.

8. The system of claim 7, further comprising a position sensor associated with the contrast return line, said position sensor comprising a pressure sensor.

9. The system of claim 7, further comprising a position sensor associated with the at least one actuatable valve.

10. The system of claim 6, wherein the at least one actuatable valve comprises a second actuatable valve fluidly coupling a saline source to the manifold.

11. The system of claim 10, further comprising a position sensor associated with the second actuatable valve.

12. The system of claim 11, wherein the position sensor comprises a pressure sensor.

13. The system of claim 11, wherein the measurement automation apparatus is configured to disregard the data generated by at least one of the injector sensor module and the reservoir sensor module based at least in part on a signal sent from the position sensor.

14. A system for measurement automation of a fluid injected into a patient with a fluid injection apparatus, the system comprising:

a reservoir;

the fluid injection apparatus comprising:
  a delivery conduit for insertion into the patient and delivery of the fluid into the patient;
  an injector for injecting the fluid into the patient via an injection fluid path fluidly coupling the injector to the delivery conduit;
  a diverter assembly disposed between the delivery conduit and the injector, said diverter assembly configured to divert at least a portion of the fluid away from an injection fluid path between the injector and the delivery conduit, the diverter assembly being fluidly coupled to the reservoir, wherein the diverter assembly is configured to allow at least the portion of the fluid injected by the injector to be simultaneously diverted away from the delivery conduit based on at least one of a pressure and a flow of the injection fluid path, wherein the diverted fluid is stored in the reservoir; and
  a connector fluidly coupling the injector to the diverter assembly and the delivery conduit;
  a manifold coupled to the injection fluid path, wherein the manifold comprises a first actuatable valve and a second actuatable valve, wherein the second actuatable valve fluidly couples a saline source to the manifold; and a measurement automation apparatus comprising:
  an injector sensor module configured to be applied the injector, wherein the injector sensor module is configured to generate data for the determination of a volume displacement within the injector;
  a reservoir sensor module configured to be applied to the reservoir, wherein the reservoir sensor module is configured to generate data for the determination of a volume displacement within the reservoir;
  a processor configured to receive the data generated by the injector sensor module and the data generated by the reservoir sensor module to determine the amount of the fluid delivered to the patient based at least in part on the data generated by the injector sensor module and the data generated by the reservoir sensor module; and
  a display operatively coupled to the processor for displaying the amount of the fluid delivered to the patient.

15. The system of claim 14, further comprising a contrast return line fluidly coupling the reservoir and the first actuatable valve.

16. The system of claim 15, further comprising a position sensor associated with the contrast return line, said position sensor comprising a pressure sensor.

17. The system of claim 15, further comprising a position sensor associated with the first actuatable valve.

18. The system of claim 14, further comprising a position sensor associated with the second actuatable valve.

19. The system of claim 18, wherein the position sensor comprises a pressure sensor.

20. The system of claim 18, wherein the measurement automation apparatus is configured to disregard the data generated by at least one of the injector sensor module and the reservoir sensor module based at least in part on a signal sent from the position sensor.

* * * * *